United States Patent
Wen et al.

(10) Patent No.: US 10,858,591 B2
(45) Date of Patent: Dec. 8, 2020

(54) STABILIZER AND LIQUID CRYSTAL COMPOSITION COMPRISING SAME

(71) Applicant: Shijiazhuang Chengzhi Yonghua Display Materials Co., Ltd, Shijiazhuang (CN)

(72) Inventors: Gang Wen, Hebei (CN); Jingsong Meng, Hebei (CN); Hongyong Shang, Hebei (CN); Limei Zhang, Hebei (CN); Guoliang Yun, Hebei (CN); Xing Zhang, Hebei (CN)

(73) Assignee: SHIJIAZHUANG CHENGZHI YONGHUA DISPLAY MATERIALS CO., LTD., Shijiazhuang (CN)

( * ) Notice: Subject to any disclaimer, the term of this patent is extended or adjusted under 35 U.S.C. 154(b) by 93 days.

(21) Appl. No.: 15/585,312

(22) Filed: May 3, 2017

(65) Prior Publication Data
US 2017/0349833 A1    Dec. 7, 2017

(30) Foreign Application Priority Data

Jun. 6, 2016    (CN) .......................... 2016 1 0392022

(51) Int. Cl.
*C09K 19/54*    (2006.01)
*C09K 19/20*    (2006.01)
(Continued)

(52) U.S. Cl.
CPC .............. *C09K 19/54* (2013.01); *C07C 39/17* (2013.01); *C07C 43/23* (2013.01); *C07C 43/253* (2013.01);
(Continued)

(58) Field of Classification Search
None
See application file for complete search history.

(56) References Cited

U.S. PATENT DOCUMENTS 3,991,139 A * 11/1976 Kokuryo ................. C08L 65/00
   524/151
6,444,278 B1 * 9/2002 Reiffenrath ............. C07B 63/04
   252/299.5
(Continued)

FOREIGN PATENT DOCUMENTS

CN    104650923 A * 5/2015
DE    19539141    4/1997
(Continued)

OTHER PUBLICATIONS

Frost et al., "Iridium-Catalyzed C4-Alkylation of 2,6-Di-tert-butylphenol by Using Hydrogen-Borrowing Catalysis", May 12, 2016, Synthesis, vol. 49, 910-916. (Year: 2016).*

(Continued)

*Primary Examiner* — Cynthia H Kelly
*Assistant Examiner* — Anna Malloy
(74) *Attorney, Agent, or Firm* — Muncy, Geissler, Olds & Lowe, P.C.

(57) ABSTRACT

A stabilizer represented by formula I, wherein M represents cyclopentyl, cyclobutyl or cyclopropyl; $Z_1$ and $Z_2$ each independently represent a single bond, —$CH_2$—, —$CH_2CH_2$—, —O—, —$CH_2O$—, —$OCH_2$— or —COO—;

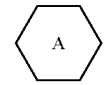

represents one or two of (Continued)

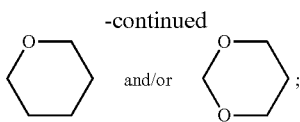

and n represents 0, 1 or 2.

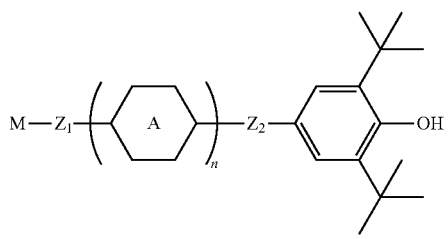

13 Claims, 2 Drawing Sheets

(51) Int. Cl.
| | |
|---|---|
| C09K 19/30 | (2006.01) |
| C09K 19/34 | (2006.01) |
| C09K 19/12 | (2006.01) |
| G02F 1/137 | (2006.01) |
| C09K 19/04 | (2006.01) |
| G02F 1/1368 | (2006.01) |
| C07C 39/17 | (2006.01) |
| C07C 43/23 | (2006.01) |
| C07C 43/253 | (2006.01) |
| C07D 309/06 | (2006.01) |
| C07D 319/06 | (2006.01) |

(52) U.S. Cl.
CPC ......... *C07D 309/06* (2013.01); *C07D 319/06* (2013.01); *C09K 19/20* (2013.01); *C09K 19/3066* (2013.01); *C09K 19/3402* (2013.01); *C07C 2601/02* (2017.05); *C07C 2601/04* (2017.05); *C07C 2601/08* (2017.05); *C07C 2601/14* (2017.05); *C09K 2019/0466* (2013.01); *C09K 2019/122* (2013.01); *C09K 2019/3009* (2013.01); *C09K 2019/3021* (2013.01); *C09K 2019/3025* (2013.01); *C09K 2019/3096* (2013.01); *C09K 2019/3422* (2013.01); *C09K 2019/3425* (2013.01); *G02F 1/1368* (2013.01); *G02F 2001/13712* (2013.01)

(56) References Cited

U.S. PATENT DOCUMENTS

| | | | | |
|---|---|---|---|---|
| 2012/0069289 | A1* | 3/2012 | Taugerbeck | ........... C09K 19/32 |
| | | | | 349/183 |
| 2015/0152330 | A1* | 6/2015 | Yun | ........................ C09K 19/30 |
| | | | | 252/299.63 |
| 2016/0131947 | A1* | 5/2016 | Park | ................... G02F 1/133711 |
| | | | | 349/128 |

FOREIGN PATENT DOCUMENTS

| | | | | |
|---|---|---|---|---|
| DE | 19539141 A1 * | 4/1997 | ............. C07B 63/04 |
| JP | 06116556 A * | 4/1994 | |
| TW | 201229217 | 7/2012 | |

OTHER PUBLICATIONS

Walton et al., "Structure-Activity Relationships for Insect Growth Regulators Derived from Substituted Di-tert-butyl phenols", 1979, Pesticide Biochemistry and Physiology, vol. 12, 23-30. (Year: 1979).*

Nishinaga et al., "Correlation between Regiospecific Dioxygen Incorporation into 2,6-Di-tert-butylphenols and Their Redox Potential", 1994, Chemistry Letters, 817-820. (Year: 1994).*

Lee et al., "Mechanism of Oxygenation of 2,6-Di-tert-butylphenol Derivative", 2006, Bull. Korean Chem. Soc.: Communications to the Editor, vol. 27, No. 1, 33-34. (Year: 2006).*

English translation of JP06116556. (Year: 1994).*

English translation of CN104650923. (Year: 2015).*

* cited by examiner

STABILIZER AND LIQUID CRYSTAL COMPOSITION COMPRISING SAME

TECHNICAL FIELD

The present invention relates to the liquid crystal display field, and specifically relates to a novel stabilizer, a liquid crystal composition comprising this stabilizer and a liquid crystal display element or liquid crystal display comprising the liquid crystal composition.

BACKGROUND

At present, the expansion of application range of liquid crystal compounds becomes broader and broader, and the liquid crystal compounds can be used in various types of displays, electro-optical devices, sensors and the like. There are a wide range of liquid crystal compounds for use in the above-mentioned display field, wherein the application of nematic phase liquid crystals is the most extensive. Nematic phase liquid crystals have been used in passive TN and STN matrix displays and systems having a TFT active matrix.

With regard to the application field of thin film transistor techniques (TFT-LCD), although the market in recent years has become very huge, and the techniques also become gradually mature, requirements of display techniques are increasing continuously, especially in terms of achieving a quick response, reducing the drive voltage for reducing power consumption, etc. Liquid crystal materials as one of important optoelectronic materials for liquid crystal displays play an important role in improving the performance of liquid crystal displays.

As liquid crystal materials, they need to have good chemical and thermal stability and stability to electric fields and electromagnetic radiations. Furthermore, as liquid crystal materials for thin film transistor techniques (TFT-LCD), they not only need to have the stabilities as above, but also should have a broader nematic phase temperature range, a suitable birefringence anisotropy, a very high electrical resistivity, a good anti-ultraviolet property, a high charge retention ratio, a low vapor pressure and other properties.

For dynamic picture display applications, the elimination of display picture ghosting and trailing requires liquid crystals to have a very quick response speed, and therefore the liquid crystals are required to have a lower rotary viscosity $\gamma_1$; moreover, for portable devices, in order to reduce the device energy consumption, it is desirable for the drive voltage of the liquid crystals to be as low as possible; and for displays for uses such as televisions, the requirements for the drive voltage of the liquid crystals are not as low as that.

At present, the environment of liquid crystal display applications also becomes diverse gradually, in addition to liquid crystal display televisions becoming a leading trend, vehicle displays, handheld computers, Pads, mobile phones etc. also gradually occupy people's lives. The service environments of such mobile devices are complex and changeable, so that the liquid crystal materials are required to have high thermal stability, high photostability, and very good chemical stability and be insensitive to temperature variations.

Simply depending on materials themselves has no longer been able to satisfy such rigorous service conditions yet. Stabilizers, such as a sterically hindered phenol stabilizer introduced in patent DE 19539141 A1, a sterically hindered amine stabilizer disclosed in TW 201229217 A, have been very early introduced into liquid crystal materials.

It is further required that the optical properties of liquid crystal materials themselves cannot be excessively destroyed or reduced while bringing about an increase of stability to liquid crystal materials. A moderate dielectric anisotropy $\Delta\varepsilon$, a moderate optical anisotropy $\Delta n$, a lower rotary viscosity $\gamma_1$ and a higher elastic constant value K, and being capable of achieving a quick response, as required for liquid crystal materials themselves cannot be lost.

SUMMARY OF THE INVENTION

With regard to the increasingly higher requirements of stabilizers for liquid crystal materials, we developed a novel stabilizer represented by formula I, which not only can improve the thermal and optical stability of the liquid crystal materials, but also has a higher clearing point and better low temperature intersolubility, and can bring about more excellent liquid crystal properties to mixed liquid crystal materials; an object of the present invention further lies in providing a liquid crystal composition and a liquid crystal display element or liquid crystal display comprising the liquid crystal composition, wherein the liquid crystal composition has a lower viscosity, can achieve a quick response, and further has a moderate dielectric anisotropy $\Delta\varepsilon$, a moderate optical anisotropy $\Delta n$, and a high stability to heat and light. The liquid crystal display element or liquid crystal display comprising the liquid crystal composition has a broader nematic phase temperature range, a suitable birefringence anisotropy, a very high electrical resistivity, a good anti-ultraviolet property, a high charge retention ratio, a low vapor pressure and the like.

For achieving the above-mentioned beneficial technical effects, the present invention provides a stabilizer represented by formula I:

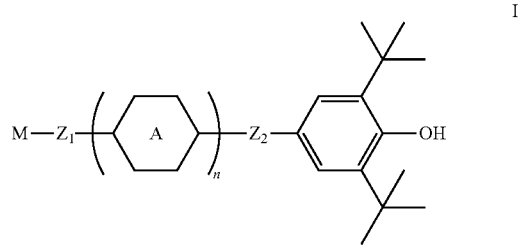

wherein M represents cyclopentyl, cyclobutyl or cyclopropyl;

$Z_1$ and $Z_2$ each independently represent a single bond, —CH$_2$—, —CH$_2$CH$_2$—, —O—, —CH$_2$O—, —OCH$_2$— or —COO—;

represents one or two of

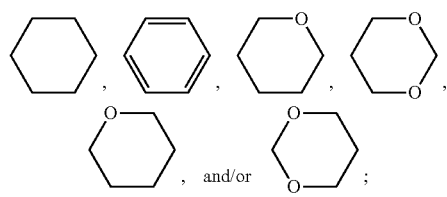

and n represents 0, 1 or 2.

The stabilizer represented by formula I is preferably selected from the following structures:

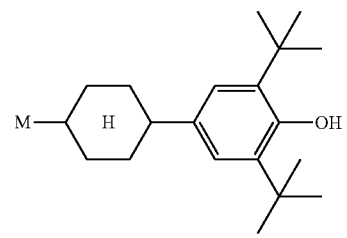
I-a

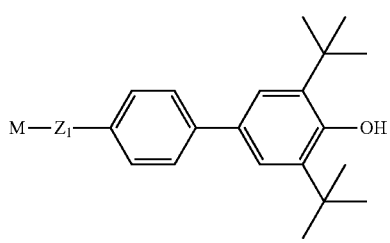
I-b

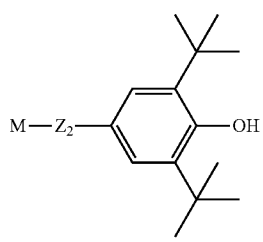
I-c wherein M represents cyclopentyl, cyclobutyl or cyclopropyl;

represents and

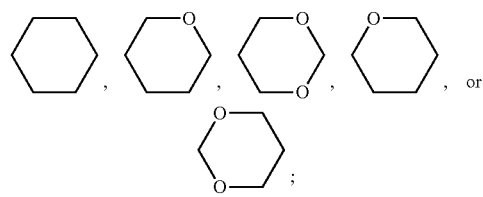
;

$Z_1$ and $Z_2$ each independently represent a single bond, —CH$_2$—, —CH$_2$CH$_2$—, —O—, —CH$_2$O—, —OCH$_2$— or —COO—.

The stabilizer represented by formula I-a is further preferably selected from the following structures:

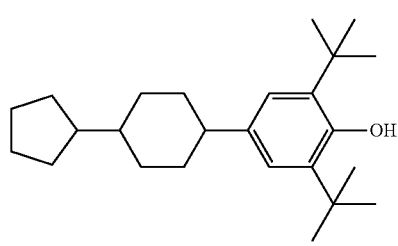
I-a-1

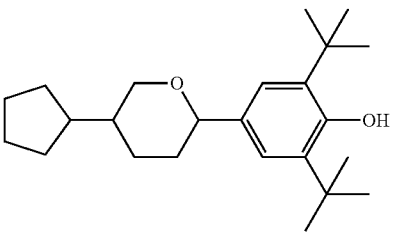
I-a-3

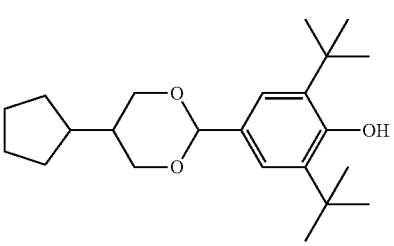
I-a-4

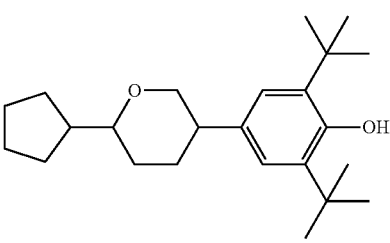
I-a-5

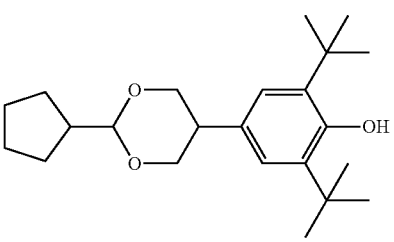
I-a-6

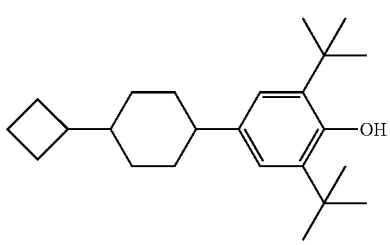
I-a-7

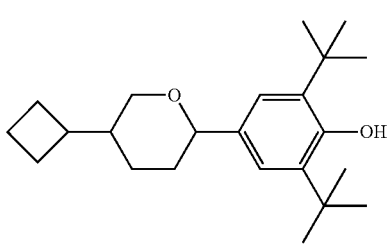
I-a-9

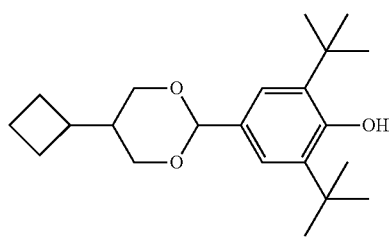 I-a-10

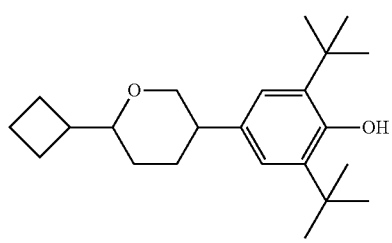 I-a-11

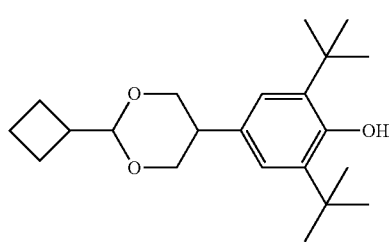 I-a-12

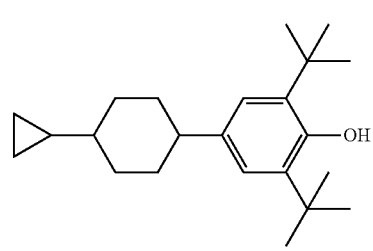 I-a-13

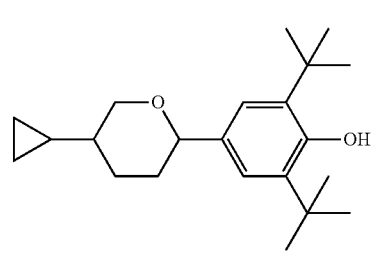 I-a-15

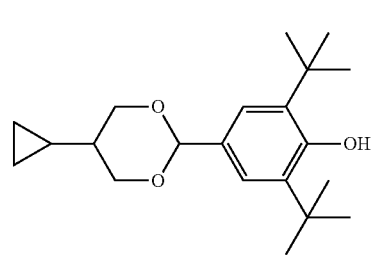 I-a-16

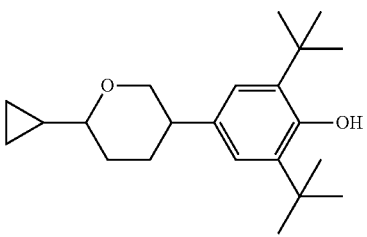 I-a-17

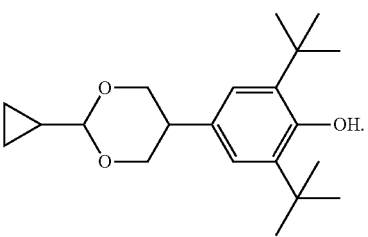 I-a-18

The stabilizer represented by formula I-b is further preferably selected from the following structures:

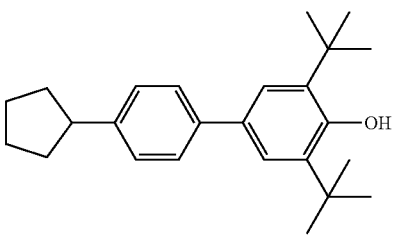 I-b-1

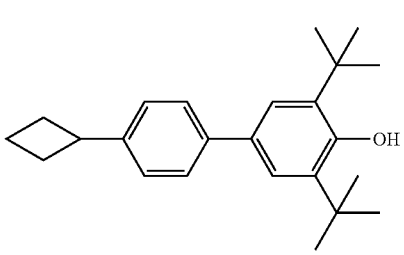 I-b-2

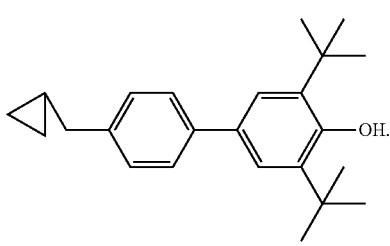 I-b-3

In addition to the excellent effect of liquid crystal-stabilizing reliability, the above-mentioned structures further provides excellent liquid crystal properties, a higher clearing point and a lower viscosity. After the addition of the above-mentioned stabilizers, the optical property of the liquid crystal itself will not become poor.

The stabilizer represented by formula I-c is further preferably selected from the following structures:

| | |
|---|---|
| 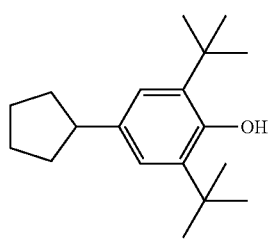 I-c-1 | 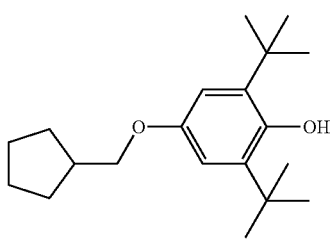 I-c-7 |
| 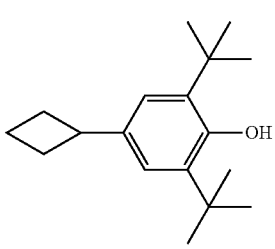 I-c-2 | 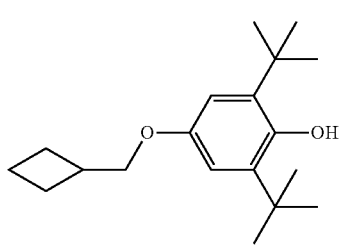 I-c-8 |
| 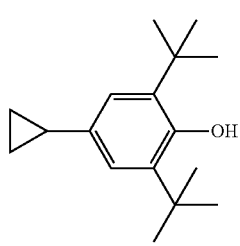 I-c-3 | 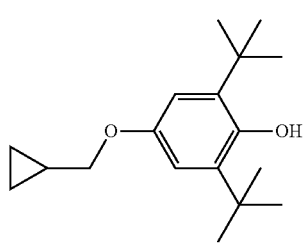 I-c-9 |
| I-c-4 | I-c-10 |
| I-c-5 | 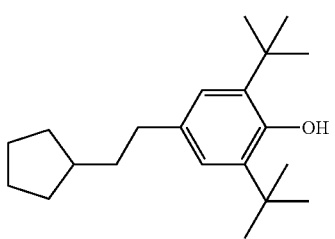 I-c-11 |
| I-c-6 | 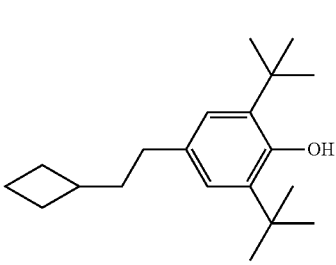 I-c-12 |
| 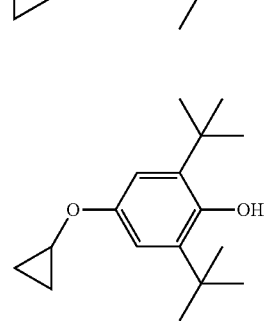 | |

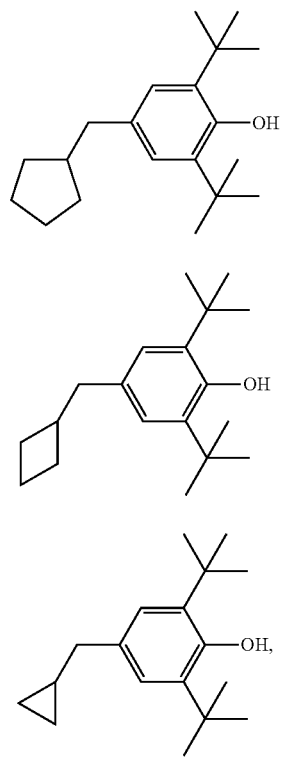

The present invention further provides a novel liquid crystal composition, and the liquid crystal composition provided by the present invention comprises one or more stabilizers as mentioned above.

The liquid crystal composition provided by the present invention may further comprise one or more of compounds of formulas II-1 to II-14:

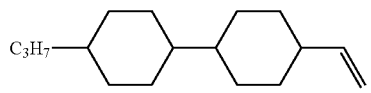
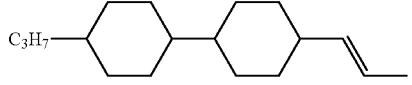
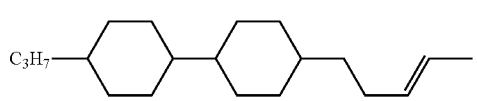
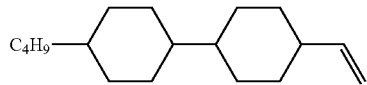
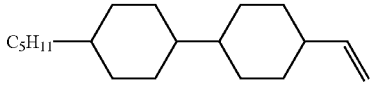
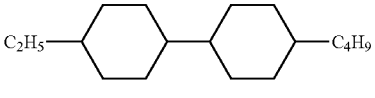
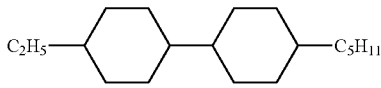
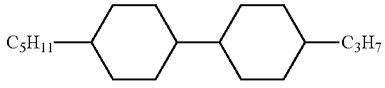
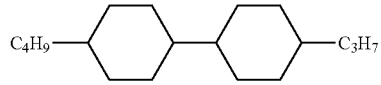
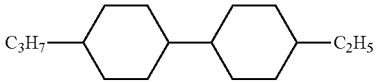
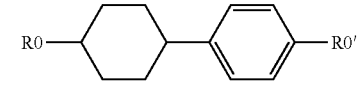
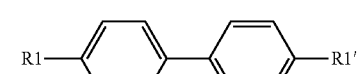
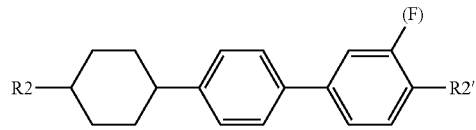
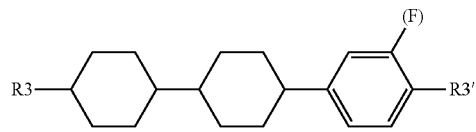

wherein R0, R0', R1, R1', R2, R2', R3, R3' each independently represent an alkyl group having a carbon atom number of 1-10, an alkenyl group having a carbon atom number of 2-10, or an alkoxy group having a carbon atom number of 1-10, wherein any —CH$_2$— can be substituted by —O—, and any hydrogen can be substituted by F; and the (F)s each independently represent H or F.

The liquid crystal composition provided by the present invention has a high value K, a low viscosity, a high clearing point and a suitable refractive index anisotropy, is particularly suitable for TFT liquid crystal display, and particularly due to its particularly superior reliability, has a very good application value in high-end IPS-TFT, VA-TFT, and PSVA-TFT liquid crystals.

As a preferred solution, in said liquid crystal composition, the total content in mass percentage of the compound represented by formula I is preferably 0.001-5%; the total content in mass percentage of the compounds represented by formulas II-1 to II-10 is preferably 1-60%; and the total content in mass percentage of the compounds represented by formulas II-11 to II-14 is preferably 0-30%, and further preferably 1-30%;

as a preference, R0 and R2 each independently represent an alkyl group having a carbon atom number of 1-5 or an alkenyl group having a carbon atom number of 2-5, and R1 and R3 each independently represent an alkyl or alkoxy group having a carbon atom number of 1-5.

The liquid crystal composition of the present invention may be a positive liquid crystal composition and may further comprise one or more compounds represented by formula III:

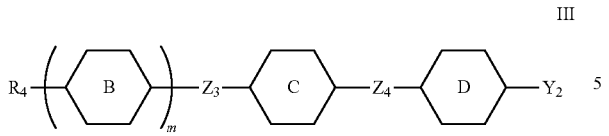

III wherein R₄ represents an alkyl group having a carbon atom number of 1-10, a fluorinated alkyl group having a carbon atom number of 1-10, an alkoxy group having a carbon atom number of 1-10, a fluorinated alkoxy group having a carbon atom number of 1-10, an alkenyl group having a carbon atom number of 2-10, a fluorinated alkenyl group having a carbon atom number of 2-10, an alkenoxy group having a carbon atom number of 3-8 or a fluorinated alkenoxy group having a carbon atom number of 3-8, and any one or more CH₂ in R₄ may be substituted by cyclopentyl, cyclobutyl or cyclopropyl;

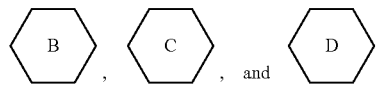

each independently represent one or two of

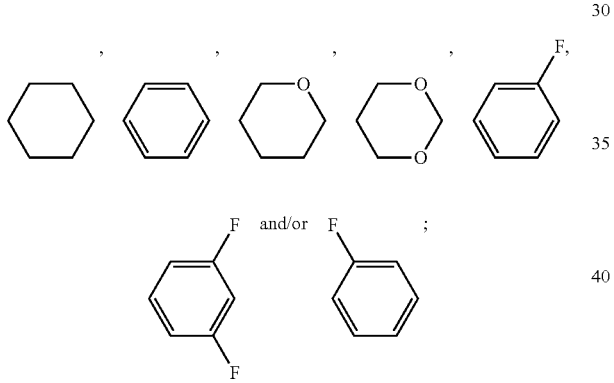

m represents 1 or 2; and

Z₃ and Z₄ each independently represent a single bond, —CF₂O—, —CH₂CH₂— or —CH₂O—; and Y₂ represents F, a fluorinated alkyl group having a carbon atom number of 1-5, a fluorinated alkoxy group having a carbon atom number of 1-5, a fluorinated alkenyl group having a carbon atom number of 2-5, or a fluorinated alkenoxy group having a carbon atom number of 3-8.

The compounds represented by formula III are preferably compounds of formulas III-1 to III-22:

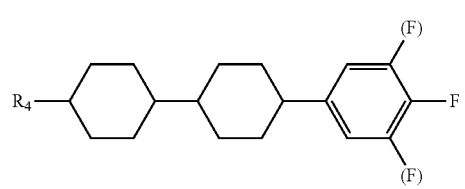

III-1

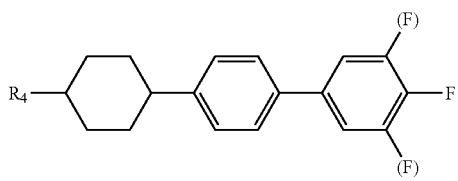

III-2

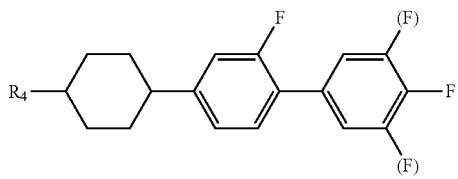

III-3

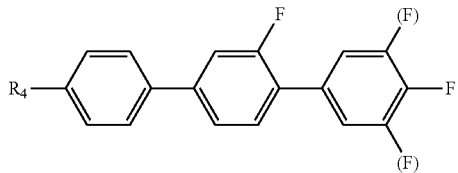

III-4

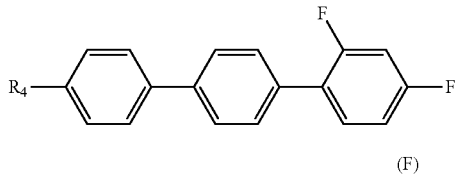

III-5

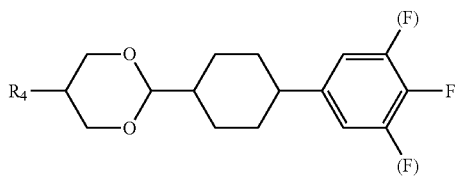

III-6

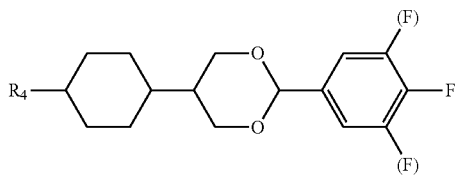

III-7

III-8

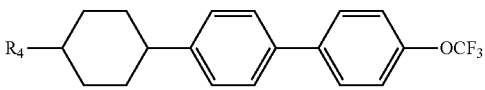

III-9

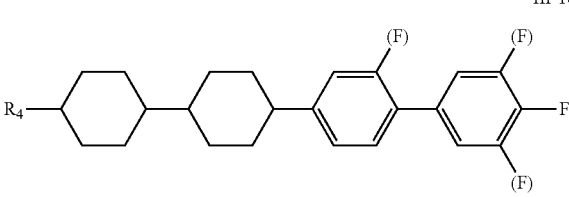

III-10

-continued

III-11
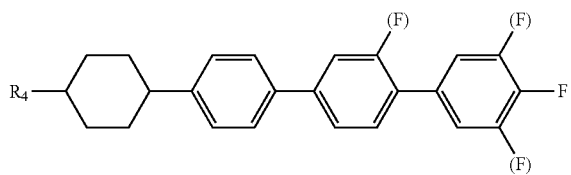

III-12
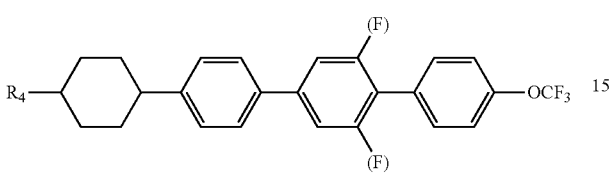

III-13
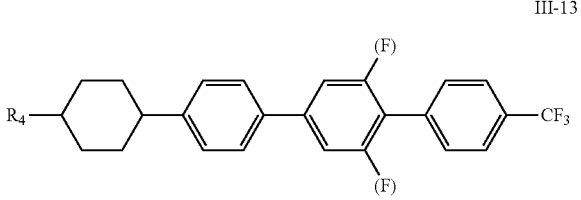

III-14
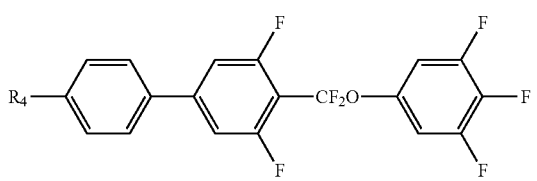

III-15
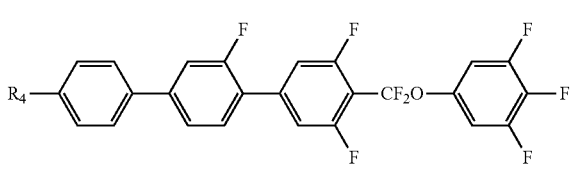

III-16
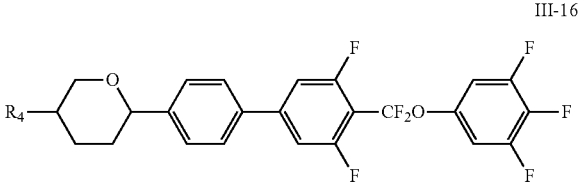

III-17
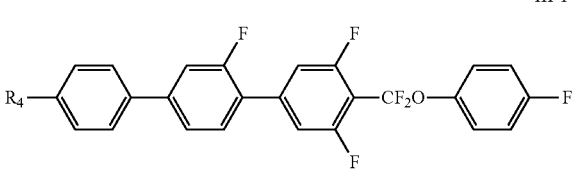

III-18
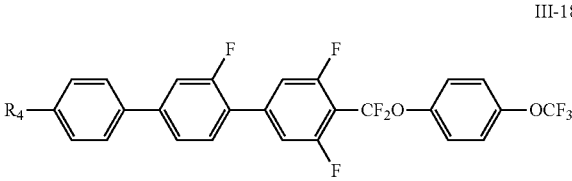

-continued

III-19
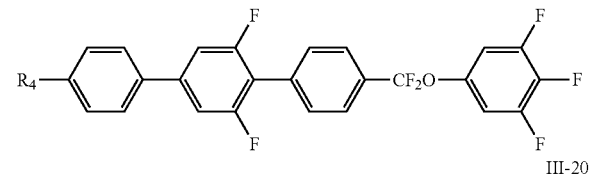

III-20, III-21, III-22
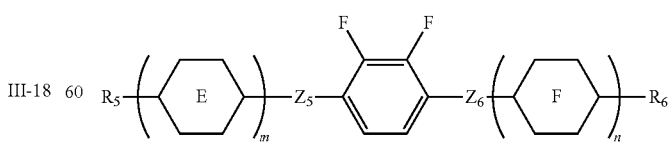

wherein $X_1$ and $X_2$ each independently represent H or F, and cannot both be F or H;

$R_4$ each independently represents an alkyl group having a carbon atom number of 1-10, a fluorinated alkyl group having a carbon atom number of 1-10, an alkoxy group having a carbon atom number of 1-10, a fluorinated alkoxy group having a carbon atom number of 1-10, an alkenyl group having a carbon atom number of 2-10, a fluorinated alkenyl group having a carbon atom number of 2-10, an alkenoxy group having a carbon atom number of 3-8 or a fluorinated alkenoxy group having a carbon atom number of 3-8, and any $CH_2$ in $R_4$ may be substituted by cyclopentyl, cyclobutyl or cyclopropyl;

the (F)s each independently represent H or F; and $Y_2$ each independently represents F, a fluorinated alkyl group having a carbon atom number of 1-5, a fluorinated alkoxy group having a carbon atom number of 1-5, a fluorinated alkenyl group having a carbon atom number of 2-5, or a fluorinated alkenoxy group having a carbon atom number of 3-8.

The liquid crystal composition provided by the present invention may be a negative liquid crystal composition and may further comprise one or more compounds represented by formula IV:

IV wherein $R_5$ and $R_6$ each independently represent an alkyl group having a carbon atom number of 1-10, a fluorinated alkyl group having a carbon atom number of 1-10, an alkoxy group having a carbon atom number of 1-10, a fluorinated alkoxy group having a carbon atom number of 1-10, an alkenyl group having a carbon atom number of 2-10, a fluorinated alkenyl group having a carbon atom number of 2-10, an alkenoxy group having a carbon atom number of 3-8 or a fluorinated alkenoxy group having a carbon atom number of 3-8, and any $CH_2$ in $R_5$ and $R_6$ may be substituted by cyclopentyl, cyclobutyl or cyclopropyl;

$Z_5$ and $Z_6$ each independently represent a single bond, —$CH_2CH_2$—, —$CH_2O$—;

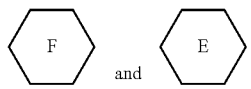

each independently represent one of

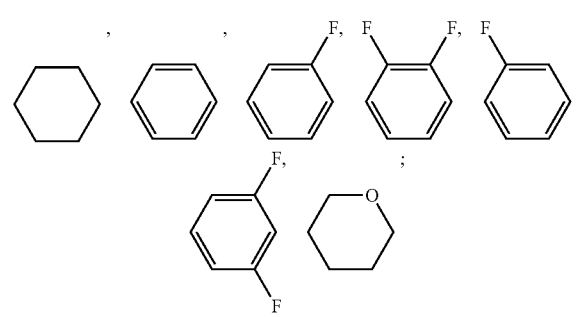

m represents 1 or 2; and n represents 0, 1 or 2.

The compounds represented by formula IV are preferably compounds of formulas IV-1 to IV-11:

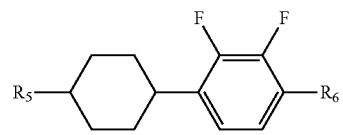 IV-1

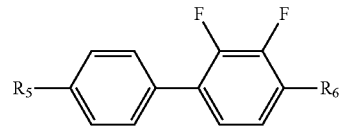 IV-2

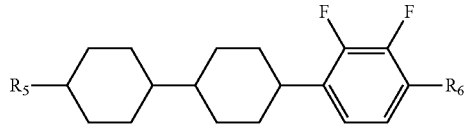 IV-3

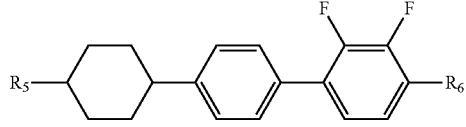 IV-4

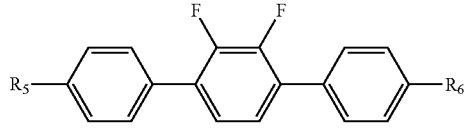 IV-5

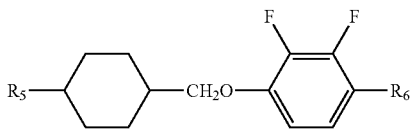 IV-6

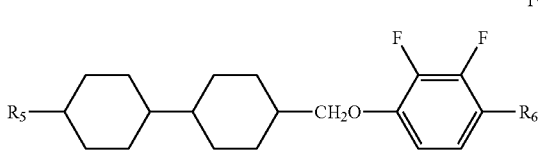 IV-7

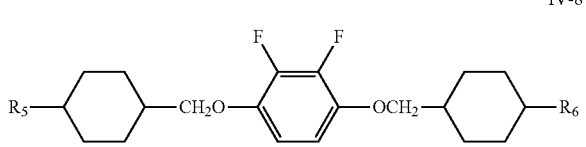 IV-8

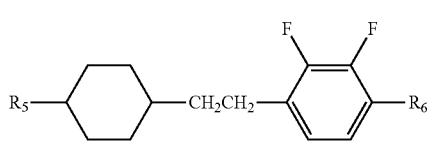 IV-9

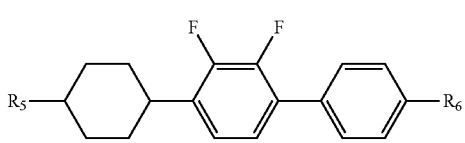 IV-10

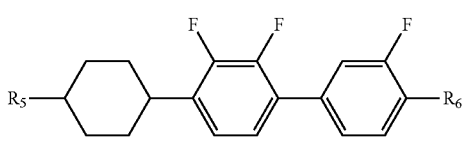 IV-11 wherein $R_5$ and $R_6$ each independently represent an alkyl group having a carbon atom number of 1-10, a fluorinated alkyl group having a carbon atom number of 1-10, an alkoxy group having a carbon atom number of 1-10, a fluorinated alkoxy group having a carbon atom number of 1-10, an alkenyl group having a carbon atom number of 2-10, a fluorinated alkenyl group having a carbon atom number of 2-10, an alkenoxy group having a carbon atom number of 3-8 or a fluorinated alkenoxy group having a carbon atom number of 3-8, and any $CH_2$ in $R_5$ and $R_6$ may be substituted by cyclopentyl, cyclobutyl or cyclopropyl.

The liquid crystal composition of the present invention may be a negative liquid crystal composition and may further comprise one or more compounds represented by formula V:

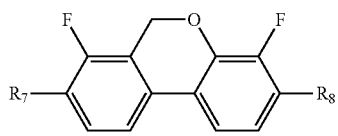 V wherein $R_7$ and $R_8$ each independently represent an alkyl group having a carbon atom number of 1-10, a fluorinated alkyl group having a carbon atom number of 1-10, an alkoxy group having a carbon atom number of 1-10, a fluorinated alkoxy group having a carbon atom number of 1-10, an alkenyl group having a carbon atom number of 2-10, a fluorinated alkenyl group having a carbon atom number of 2-10, an alkenoxy group having a carbon atom number of 3-8 or a fluorinated alkenoxy group having a carbon atom number of 3-8, and any $CH_2$ in $R_7$ and $R_8$ may be substituted by cyclopentyl, cyclobutyl or cyclopropyl.

The compounds represented by formula V are preferably

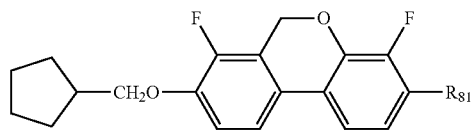

$R_{81}$ represents an alkoxy group having a carbon atom number of 1-10.

The liquid crystal compositions in different ratios of components will exhibit slightly different properties, such as a dielectric anisotropy $\Delta\in$, an optical anisotropy $\Delta n$, a transition temperature point CP when the nematic phase of the liquid crystal transforms into a liquid, stability at low temperatures, which all may be different, and can be used in different types of display devices, but have the same characteristic that the rotary viscosities $\gamma_1$ thereof are lower. The application to liquid crystal display devices can achieve a quick response.

To the liquid crystal compound provided by the present invention, a chiral additive may be further added.

The chiral additive is preferably (levorotary or dextrorotary):

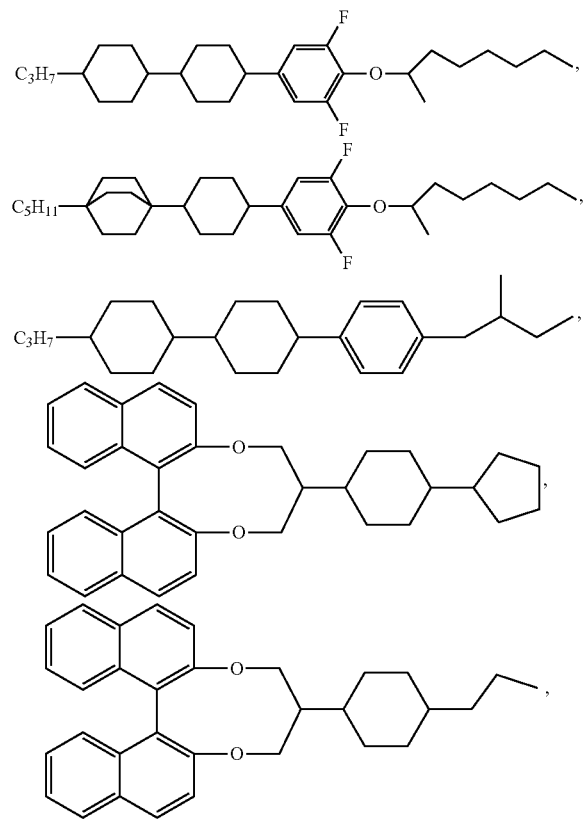

The present invention further relates to a liquid crystal display element or liquid crystal display comprising any liquid crystal composition as mentioned above; and said liquid crystal display element or liquid crystal display is an active matrix display element or display or a passive matrix display element or display.

Said liquid crystal display element or liquid crystal display is preferably an active matrix addressing liquid crystal display element or liquid crystal display.

Said active matrix display element or display is specifically a TN-TFT or IPS-TFT liquid crystal display element or display.

The liquid crystal composition provided by the present invention has a lower viscosity, can achieve a quick response, and further has a moderate dielectric anisotropy $\Delta\in$, a moderate optical anisotropy $\Delta n$, and a high stability to heat and light.

Liquid crystal materials comprising the liquid crystal composition provided by the present invention not only have good chemical and thermal stability, but also have stability to electric fields and electromagnetic radiations. Furthermore, as liquid crystal materials for thin film transistor techniques (TFT-LCD), they further have a broader nematic phase temperature range, a suitable birefringence anisotropy, a very high electrical resistivity, a good anti-ultraviolet property, a high charge retention ratio, a low vapor pressure and other properties.

DESCRIPTION OF EMBODIMENTS

Figure 1:
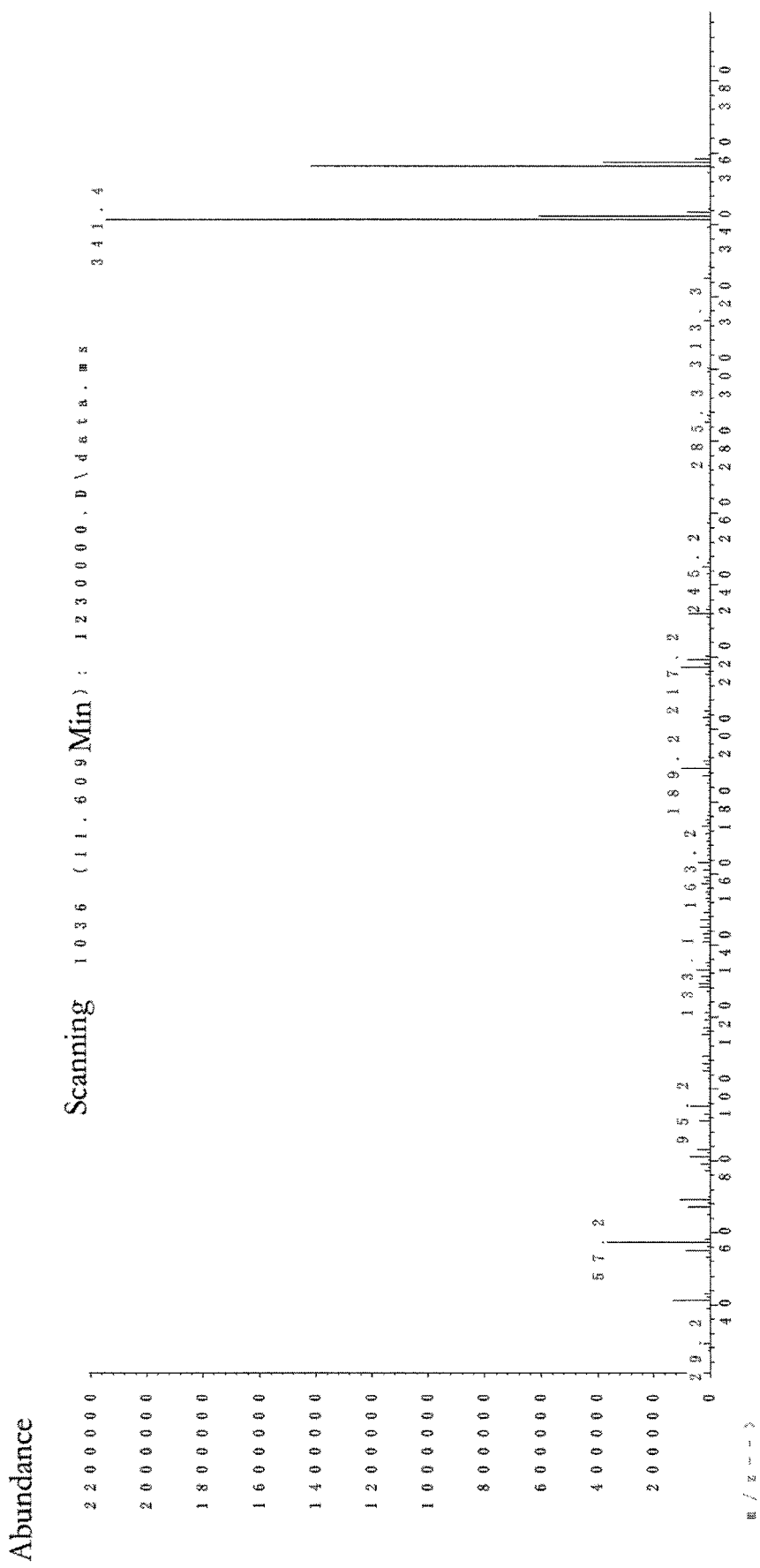
FIG. 1 is a mass spectrum of a compound represented by formula I-a-1.
Figure 2:
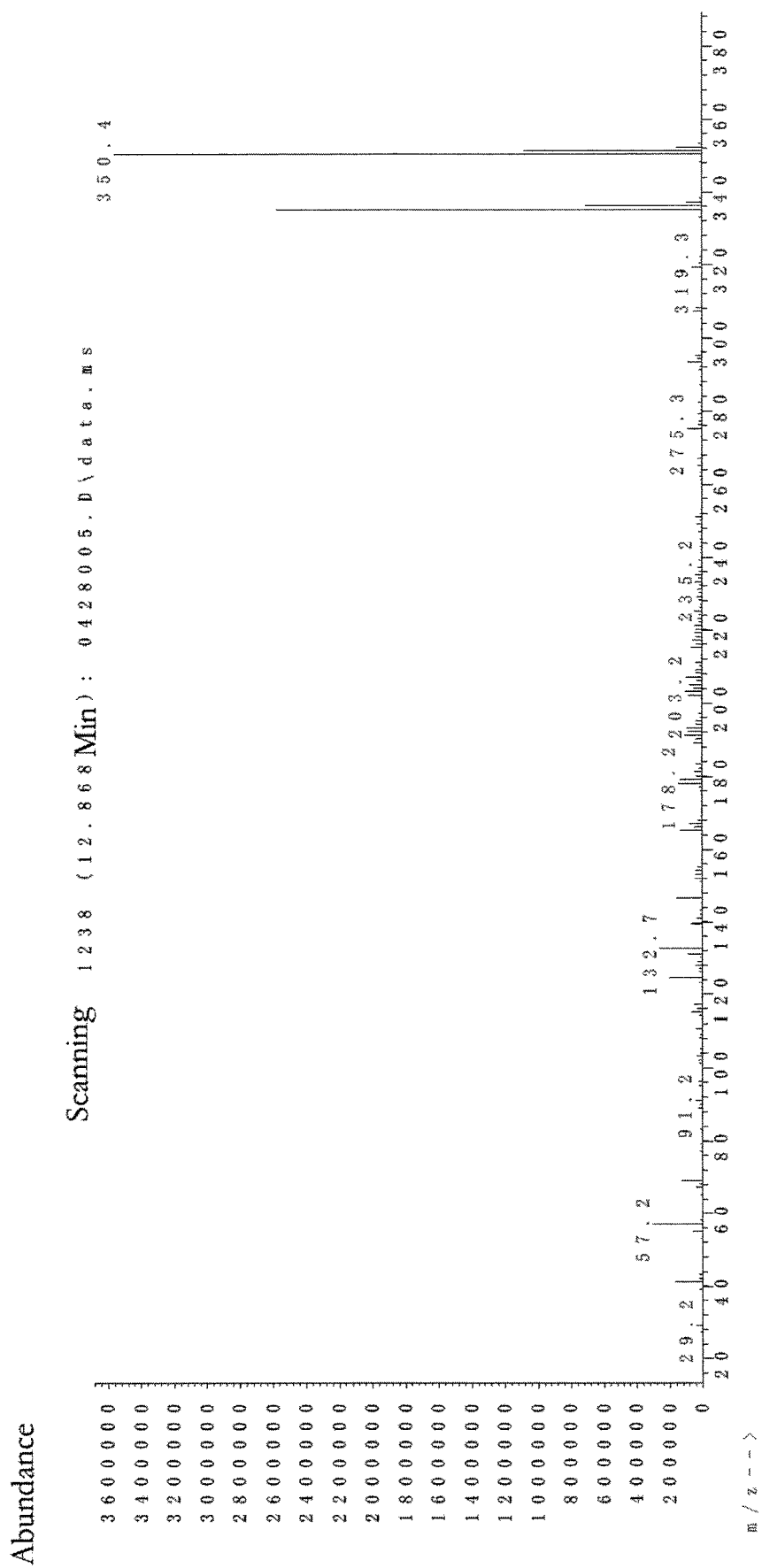
FIG. 2 is a mass spectrum of a compound represented by formula I-b-1.

The present invention is further described in conjunction with particular examples below, and the present invention is not limited to the following examples. Said methods are all conventional methods, unless otherwise specified. Said raw materials can all be obtained from disclosed commercial approaches, unless otherwise specified. Said percentages are all mass percentages, unless otherwise specified.

In the following examples,

CP represents a clearing point, directly determined by WRX-1S microscopic thermal analyzer, with a temperature rate set to be 3° C./min.

$\Delta n$ represents an optical anisotropy (589 nm, 20° C.), $\Delta\in$ represents a dielectric anisotropy (25° C., 1 KHz, HP4284A, 5.2 micron TN levorotary box), $\gamma_1$ represents a rotary viscosity (mPa·s) at 20° C., VHR (%) represents a charge retention ratio (5 V, 60 Hz, 20° C.), and $\rho(\times 10^{13} \Omega \cdot cm)$ represents electrical resistivity (at 20° C.).

Testers for the charge retention ratio VHR (%) and the electrical resistivity $\rho(\times 10^{13} \Omega \cdot cm)$ are both TOYO06254 and TOYO6517-type liquid crystal physical property evaluation systems (at a test temperature of 20° C., a time of 16 ms, and a test box of 7.0 microns).

In the reaction process, the reaction progress is generally monitored by means of TLC, and treatments after the completion of the reaction are generally water washing, extraction, organic phase combination and drying, solvent evaporation under reduced pressure, as well as recrystallization and column chromatography; and a person skilled in the art would be able to implement the present invention according to the following description.

In the examples of the present invention application, liquid crystal monomer structures are represented by codes, wherein the code representation methods of cyclic structures, end groups and linking groups of the liquid crystals are shown in tables (I) and (II) below

TABLE (I)

Codes corresponding to cyclic structures

| Cyclic structures | Corresponding codes |
|---|---|
|  | C |
|  | B |
| 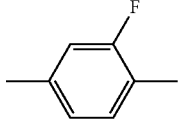 | B(3F) |
| 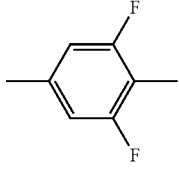 | B(3F, 5F) |
| 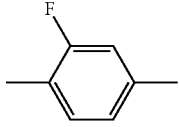 | B(2F) |
| 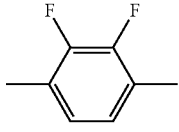 | B(2F, 3F) |
| 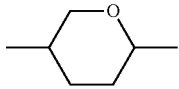 | C[3O] |
|  | C[3O, 5O] |
| 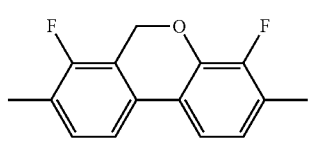 | Sa |

TABLE (II)

Codes corresponding to end groups and linking groups

| End groups and linking groups | Corresponding codes |
|---|---|
| $C_nH_{2n+1}$— | n- |
| $C_nH_{2n+1}O$— | nO— |
| —$OCF_3$ | —$OCF_3$ |

TABLE (II)-continued

Codes corresponding to end groups and linking groups

| End groups and linking groups | Corresponding codes |
|---|---|
| —$CF_2O$— | —$CF_2O$— |
| —F | —F |
| —CN | —CN |
| —$CH_2CH_2$— | —E— |
| —CH=CH— | —V— |
| —C≡C— | —W— |
| —COO— | —COO— |
| —CH=CH—$C_nH_{2n+1}$ | Vn— |
| 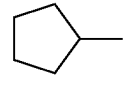 | C(5)— |
| 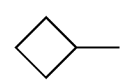 | C(4)— |
| 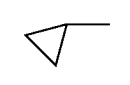 | C(3)— |

EXAMPLES

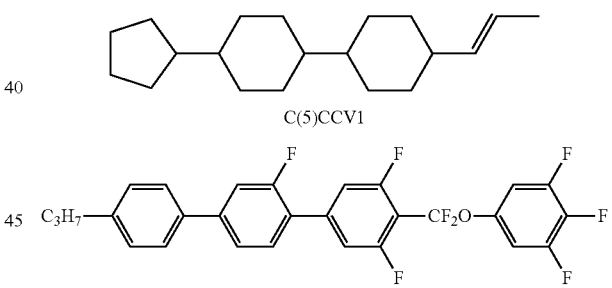

C(5)CCV1

3B B(3F) B(3F,5F) $CF_2O$ B(3F,5F)F

Route:

Example 1

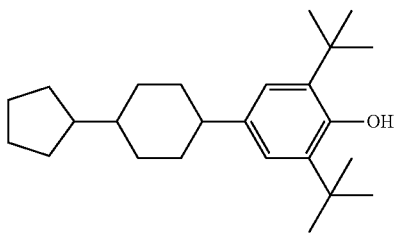
I-a-1

Route:

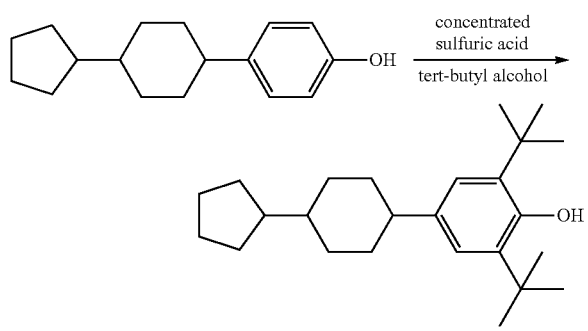

Operation Procedure:

To a 2 L three-necked flask, 4-cyclopentyl cyclohexyl phenol (95 g, 0.389 mol) and 500 ml of petroleum ether are added and stirred for 5 min, 39 g of concentrated sulfuric acid is added, the temperature is raised to 70° C. (in a water bath), a mixed liquid of tert-butyl alcohol (151 g, 2.04 mol) and 100 ml of petroleum ether are added dropwise for an addition time of 2 h, the temperature is controlled at 70-72° C., and after the completion of the addition, the temperature is maintained for 4 h; and liquid separation is directly carried out to separate sulfuric acid, 300 ml of water and 1 L of EA are added and stirred for 5 min, liquid separation is carried out, the organic phase is directly dried in a rotary manner, the product is dissolved under heat in 1 fold of petroleum ether and 3 folds of ethanol, chilled in a refrigerator for 6 hours, and subjected to suction filtration, and after repeated crystallization 3 times, 57 g is obtained, with GC: 99.88% and a yield of 40%.

Example 2

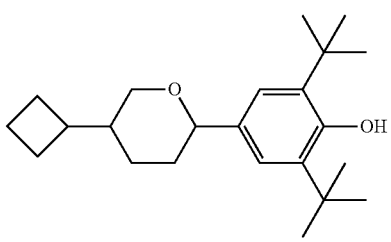
I-a-9

Route:

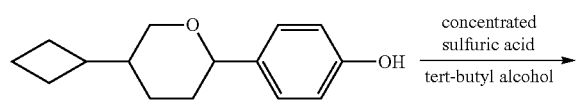

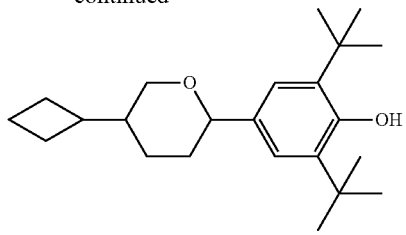

To a 2 L three-necked flask, 4-(5'-cyclobutyltetrahydropyrane)phenol (93 g, 0.4 mol) and 500 ml of petroleum ether are added and stirred for 5 min, 39 g of concentrated sulfuric acid is added, the temperature is raised to 70° C. (in a water bath), a mixed liquid of tert-butyl alcohol (151 g, 2.04 mol) and 100 ml of petroleum ether are added dropwise for an addition time of 2 h, the temperature is controlled at 70-72° C., and after the completion of the addition, the temperature is maintained for 4 h; and liquid separation is directly carried out to separate sulfuric acid, 300 ml of water and 1 L of ethyl acetate are added and stirred for 5 min, liquid separation is carried out, the organic phase is directly dried in a rotary manner, the product is dissolved under heat in 1 fold of petroleum ether and 3 folds of ethanol, chilled in a refrigerator for 6 hours, and subjected to suction filtration, and after repeated crystallization 4 times, 50 g is obtained, with GC: 99.66% and a yield of 35%.

Example 3

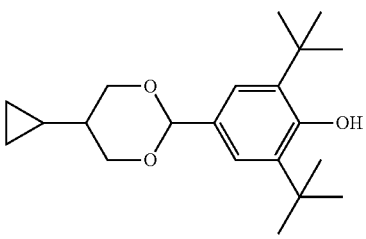
I-a-16

Route:

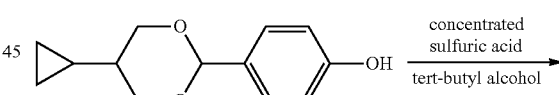

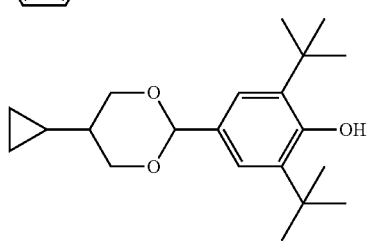

To a 1 L three-necked flask, 4-(5'-cyclopropyl-1',3'-dioxane)phenol (44 g, 0.2 mol) and 300 ml of petroleum ether are added and stirred for 5 min, 20 g of concentrated sulfuric acid is added, the temperature is raised to 70° C. (in a water bath), a mixed liquid of tert-butyl alcohol (74 g, 1 mol) and 50 ml of petroleum ether are added dropwise for an addition time of 2 h, the temperature is controlled at 70-72° C., and after the completion of the addition, the temperature is maintained for 4 h; and liquid separation is directly carried out to separate sulfuric acid, 200 ml of water and 500 mL of ethyl acetate are added and stirred for 5 min, liquid separation is carried out, the organic phase is directly dried in a rotary manner, the product is dissolved under heat in 1 fold of petroleum ether and 3 folds of ethanol, chilled in a refrigerator for 6 hours, and subjected to suction filtration, and after repeated crystallization 4 times, 33 g is obtained, with GC: 99.5% and a yield of 50%.

Example 4

I-b-1

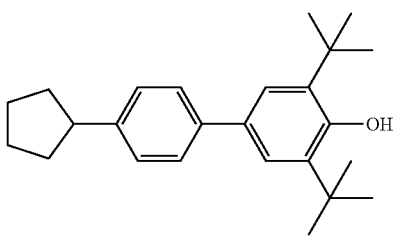

Route:

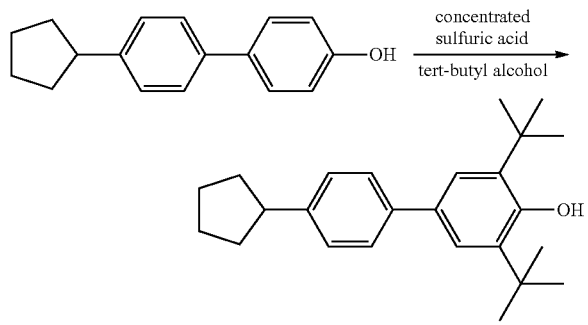

To a 1 L three-necked flask, 4'-cyclopentyl-4-hydroxy-1,1'-biphenyl (47.6 g, 0.2 mol) and 300 ml of petroleum ether are added and stirred for 5 min, 20 g of concentrated sulfuric acid is added, the temperature is raised to 70° C. (in a water bath), a mixed liquid of tert-butyl alcohol (74 g, 1 mol) and 50 ml of petroleum ether are added dropwise for an addition time of 2 h, the temperature is controlled at 70-72° C., and after the completion of the addition, the temperature is maintained for 4 h; and liquid separation is directly carried out to separate sulfuric acid, 200 ml of water and 500 mL of ethyl acetate are added and stirred for 5 min, liquid separation is carried out, the organic phase is directly dried in a rotary manner, the product is dissolved under heat in 1 fold of petroleum ether and 3 folds of ethanol, chilled in a refrigerator for 6 hours, and subjected to suction filtration, and after repeated crystallization 4 times, 60 g is obtained, with GC: 99.9% and a yield of 85%.

Example 5

I-c-3

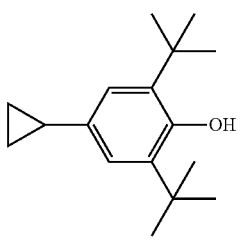

Route:

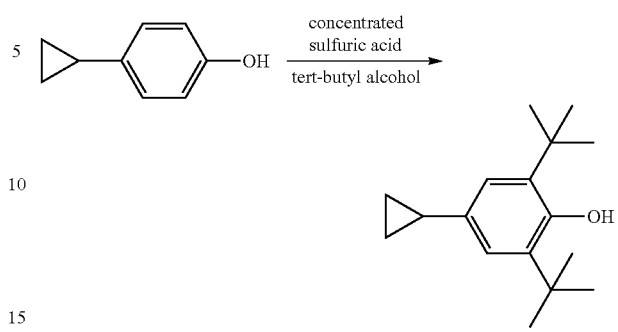

To a 2 L three-necked flask, 4-cyclopropylphenol (53.6 g, 0.4 mol) and 500 ml of petroleum ether are added and stirred for 5 min, 39 g of concentrated sulfuric acid is added, the temperature is raised to 70° C. (in a water bath), a mixed liquid of tert-butyl alcohol (151 g, 2.04 mol) and 100 ml of petroleum ether are added dropwise for an addition time of 2 h, the temperature is controlled at 70-72° C., and after the completion of the addition, the temperature is maintained for 4 h; and liquid separation is directly carried out to separate sulfuric acid, 300 ml of water and 1 L of ethyl acetate are added and stirred for 5 min, liquid separation is carried out, the organic phase is directly dried in a rotary manner, the product is dissolved under heat in 1 fold of petroleum ether and 3 folds of ethanol, chilled in a refrigerator for 6 hours, and subjected to suction filtration, and after repeated crystallization 3 times, 40 g is obtained, with GC: 99.6% and a yield of 40%.

Example 6

I-c-4

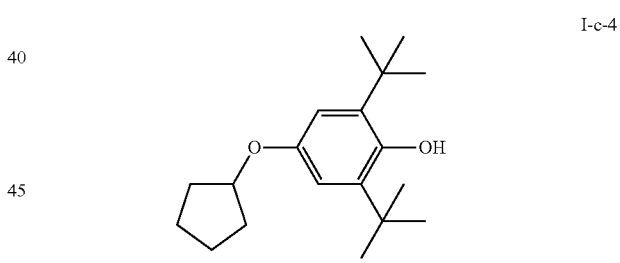

Route:

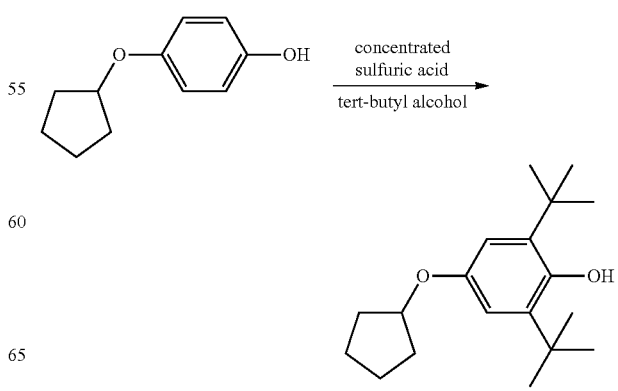

To a 1 L three-necked flask, 4-(cyclopentyloxy)phenol (35.6 g, 0.2 mol) and 300 ml of petroleum ether are added and stirred for 5 min, 20 g of concentrated sulfuric acid is added, the temperature is raised to 70° C. (in a water bath), a mixed liquid of tert-butyl alcohol (74 g, 1 mol) and 50 ml of petroleum ether are added dropwise for an addition time of 2 h, the temperature is controlled at 70-72° C., and after the completion of the addition, the temperature is maintained for 4 h; and liquid separation is directly carried out to separate sulfuric acid, 200 ml of water and 500 mL of ethyl acetate are added and stirred for 5 min, liquid separation is carried out, the organic phase is directly dried in a rotary manner, the product is dissolved under heat in 1 fold of petroleum ether and 3 folds of ethanol, chilled in a refrigerator for 6 hours, and subjected to suction filtration, and after repeated crystallization 4 times, 29 g is obtained, with GC: 99.75% and a yield of 50%.

Example 7

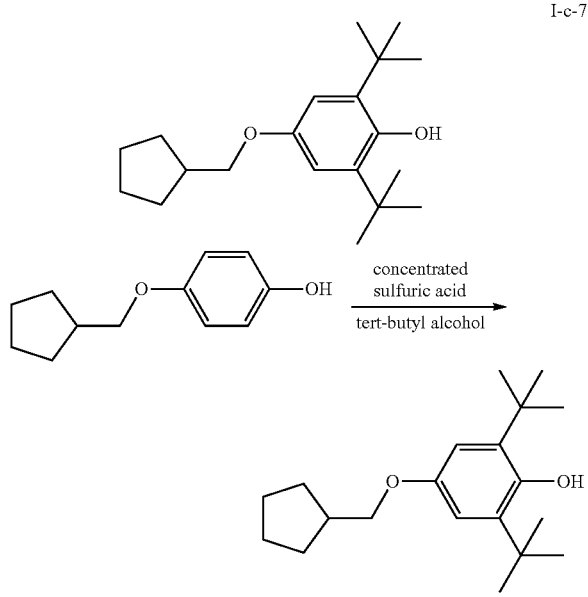

I-c-7

To a 1 L three-necked flask, 4-(cyclopentylmethoxy)phenol (38.4 g, 0.2 mol) and 300 ml of petroleum ether are added and stirred for 5 min, 20 g of concentrated sulfuric acid is added, the temperature is raised to 70° C. (in a water bath), a mixed liquid of tert-butyl alcohol (74 g, 1 mol) and 50 ml of petroleum ether are added dropwise for an addition time of 2 h, the temperature is controlled at 70-72° C., and after the completion of the addition, the temperature is maintained for 4 h; and liquid separation is directly carried out to separate sulfuric acid, 200 ml of water and 500 mL of ethyl acetate are added and stirred for 5 min, liquid separation is carried out, the organic phase is directly dried in a rotary manner, the product is dissolved under heat in 1 fold of petroleum ether and 3 folds of ethanol, chilled in a refrigerator for 6 hours, and subjected to suction filtration, and after repeated crystallization 4 times, 27.4 g is obtained, with GC: 99.65% and a yield of 45%.

Example 8

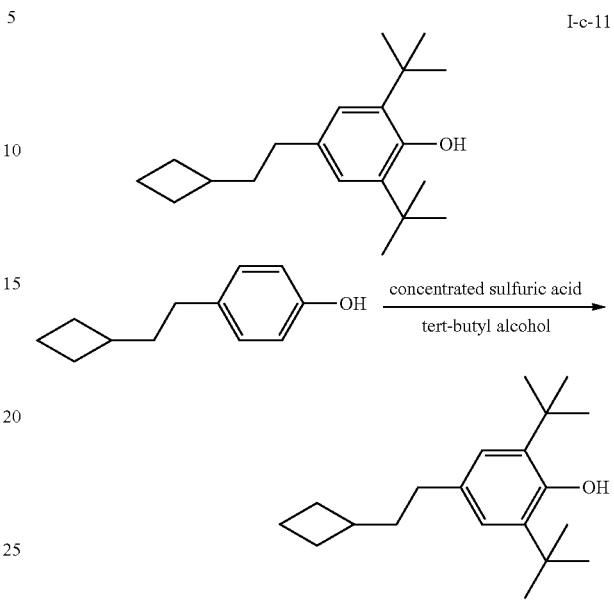

I-c-11

To a 2 L three-necked flask, 4-cyclobutylethylphenol (70.4 g, 0.4 mol) and 500 ml of petroleum ether are added and stirred for 5 min, 39 g of concentrated sulfuric acid is added, the temperature is raised to 70° C. (in a water bath), a mixed liquid of tert-butyl alcohol (151 g, 2.04 mol) and 100 ml of petroleum ether are added dropwise for an addition time of 2 h, the temperature is controlled at 70-72° C., and after the completion of the addition, the temperature is maintained for 4 h; and liquid separation is directly carried out to separate sulfuric acid, 300 ml of water and 1 L of ethyl acetate are added and stirred for 5 min, liquid separation is carried out, the organic phase is directly dried in a rotary manner, the product is dissolved under heat in 1 fold of petroleum ether and 3 folds of ethanol, chilled in a refrigerator for 6 hours, and subjected to suction filtration, and after repeated crystallization 3 times, 48.4 g is obtained, with GC: 99.7% and a yield of 42%.

Example 9

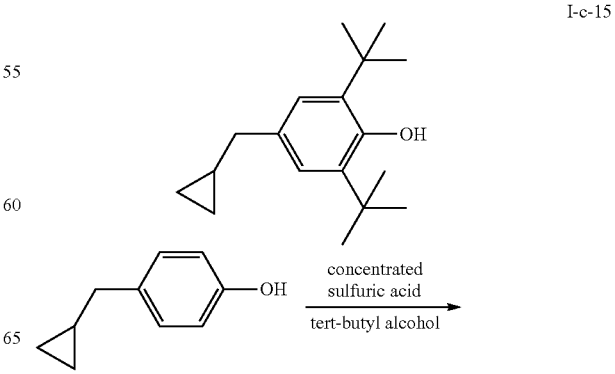

I-c-15

-continued

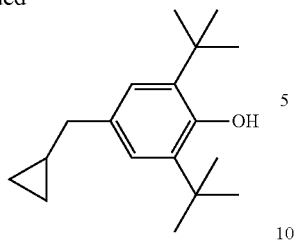

To a 2 L three-necked flask, 4-cyclopropylmethylphenol (59.2 g, 0.4 mol) and 500 ml of petroleum ether are added and stirred for 5 min, 39 g of concentrated sulfuric acid is added, the temperature is raised to 70° C. (in a water bath), a mixed liquid of tert-butyl alcohol (151 g, 2.04 mol) and 100 ml of petroleum ether are added dropwise for an addition time of 2 h, the temperature is controlled at 70-72° C., and after the completion of the addition, the temperature is maintained for 4 h; and liquid separation is directly carried out to separate sulfuric acid, 300 ml of water and 1 L of ethyl acetate are added and stirred for 5 min, liquid separation is carried out, the organic phase is directly dried in a rotary manner, the product is dissolved under heat in 1 fold of petroleum ether and 3 folds of ethanol, chilled in a refrigerator for 6 hours, and subjected to suction filtration, and after repeated crystallization 3 times, 41.6 g is obtained, with GC: 99.6% and a yield of 40%.

The following liquid crystal compositions are used as matrix MUTY

| Liquid crystal monomer codes | Content (%) |
| --- | --- |
| 3CCV | 10 |
| 2CCB(3F)O1 | 6 |
| 2CCBO1 | 6 |
| 1BB5 | 8 |
| 3CBO2 | 6 |
| 3CCB(3F)2 | 6 |
| 3CCB2 | 5 |
| 2CCB(3F,4F) | 12 |
| 2CCBOCF3 | 8 |
| C(5)BB(3F,5F)CF$_2$OB(3F,4F,5F) | 17 |
| C(5)C(3O)BB(3F,5F)CF$_2$OB(3F,4F,5F) | 6 |
| 3CCBB(3F,4F) | 5 |
| 2CBB(2F)B3 | 5 |

500 ppm of stabilizers with different structures are added respectively, after the perfusion into a liquid crystal cell, a UV irradiation (5000 mJ) experiment is carried out, a preservative experiment of maintaining at a high heat of 120° C. for three hours is carried out, and the VHR data thereof are tested, as follows for comparison:

| Sample name | VHR (%, 5 V, 60 Hz) | |
| --- | --- | --- |
| | Initial | After high temperature |
| MUTY | 99.83 | 99.22 |
| MUTY + BHT | 99.77 | 99.57 |
| MUTY + T001 | 99.78 | 99.28 |
| MUTY + I-a-1 | 99.80 | 99.77 |
| MUTY + I-b-1 | 99.79 | 99.76 |
| MUTY + I-a-9 | 99.76 | 99.68 |
| MUTY + I-a-16 | 99.77 | 99.72 |
| MUTY + I-c-11 | 99.77 | 99.65 | wherein BHT represents

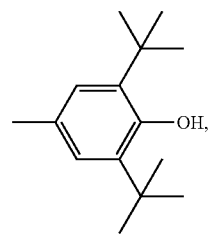 [SMILES: Cc1cc(C(C)(C)C)c(O)c(C(C)(C)C)c1]

and
T001 represents

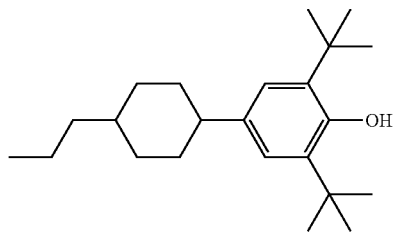 [SMILES: CCCC1CCC(c2cc(C(C)(C)C)c(O)c(C(C)(C)C)c2)CC1]

It can be seen from the above table that the stabilizer provided by the present invention, having a greater advantage with respect to the prior art, can provide better thermal resistance for a mixed liquid crystal, so as to provide a better guarantee for satisfying increasingly high reliability requirements of mixed liquid crystals for TFT display.

The compounds represented by formula I provided by the examples of the present invention, as additives applied to liquid crystal compositions, are added additionally into the components of the liquid crystal compositions, for example, the addition of 1% of formula I-a-1 is represented as follows:
  Other components: 100%, and
  Formula I-a-1: 1%.

Example 10

| Category | Liquid crystal monomer codes | Content (%) |
| --- | --- | --- |
| II | 3CCV | 10 |
| II | 2CCB(3F)O1 | 6 |
| II | 2CCBO1 | 6 |
| II | 1BB5 | 8 |
| II | 3CBO2 | 6 |
| II | 3CCB(3F)2 | 6 |
| II | 3CCB2 | 5 |
| III | 2CCB(3F, 4F) | 12 |
| III | 2CCBOCF3 | 8 |
| III | C(5)BB(3F, 5F)CF$_2$OB(3F, 4F, 5F) | 17 |
| III | C(5)C(3O)BB(3F, 5F)CF$_2$OB(3F, 4F, 5F) | 6 |
| III | 3CCBB(3F, 4F) | 5 |
| III | 2CBB(2F)B3 | 5 |
| I | 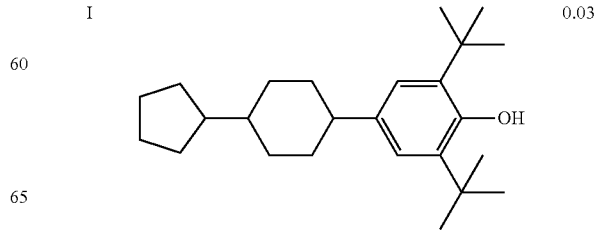 | 0.03 |

-continued

| Category | Liquid crystal monomer codes | Content (%) |
|---|---|---|
| | Δε [1 KHz, 20° C.]: 8.4 | |
| | Δn [589 nm, 20° C.]: 0.12 | |
| | Cp: 108° C. | |
| | γ₁: 99 mPa.s. | |

Example 11

| Category | Liquid crystal monomer codes | Content (%) |
|---|---|---|
| II | 3CC2 | 23 |
| II | 3CCV1 | 12 |
| II | 3CCB(2F)2 | 4 |
| II | 3CCB2 | 3 |
| II | 3CCB(3F)2 | 4 |
| II | 3CBB2 | 4 |
| III | 2CCB(3F, 4F, 5F) | 9 |
| III | 2CBB(3F, 4F, 5F) | 8 |
| II | V2CCB1 | 10 |
| III | C(3)1BBB(3F, 5F)CF₂OB(3F, 4F, 5F) | 17 |
| III | 4BB(3F)B(3F, 5F)CF₂OB(3F, 4F, 5F) | 6 |
| I | 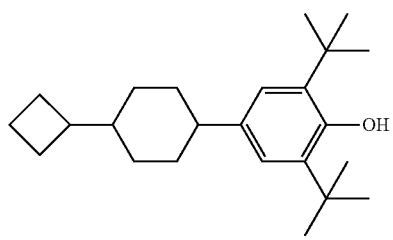 | 1 |

Δε [1 KHz, 20° C.]: 7.0
Δn [589 nm, 20° C.]: 0.09
Cp: 62° C.
γ₁: 70 mPa.s.

Example 12

| Category | Liquid crystal monomer codes | Content (%) |
|---|---|---|
| II-B | 3CC2 | 20 |
| II-B | 3CCV | 18 |
| II | 3CBO2 | 2 |
| II | VCCB(3F)2 | 5 |
| II | VCCB1 | 5 |
| III | 2CCB(3F, 4F) | 12 |
| III | 2CBBOCF3 | 8 |
| III | C(3)1BBB(3F, 5F)CF₂OB(3F, 4F, 5F) | 17 |
| III | 3BB(3F, 5F)CF₂OB(3F, 4F, 5F) | 6 |
| II | 3CBBC3 | 7 |
| I | 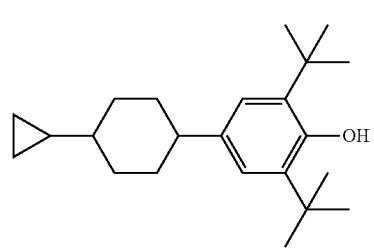 [SMILES: CC(C)(C)c1cc(C2CCC(C3CC3)CC2)cc(C(C)(C)C)c1O] | 0.05 |

-continued

| Category | Liquid crystal monomer codes | Content (%) |
|---|---|---|
| | Δε [1 KHz, 20° C.]: 6.3 | |
| | Δn [589 nm, 20° C.]: 0.090 | |
| | Cp: 81° C. | |
| | γ₁: 81 mPa.s. | |

Example 13

| Category | Liquid crystal monomer codes | Content (%) |
|---|---|---|
| II | 3CC2 | 30 |
| II | 3CCV | 20 |
| II | VCCB(3F)2 | 2 |
| II | V2CCB1 | 3 |
| III | 5BBB(2F, 4F) | 13 |
| III | C(5)BB(3F, 5F)CF₂OB(3F, 4F, 5F) | 17 |
| III | C(5)BB(3F, 5F)B(3F, 5F)CF₂OB(3F, 4F, 5F) | 6 |
| III | C(5)BBB(3F)B(3F, 4F, 5F) | 1 |
| | 1928 | |
| III | C(5)CBB(3F)B(3F, 4F, 5F)1912 | 3 |
| III | 3CBB(3F, 5F)BOCF3 | 5 |
| I | 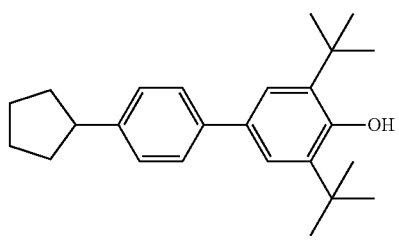 | 5 |

Δε [1 KHz, 20° C.]: 6.9
Δn [589 nm, 20° C.]: 0.115
Cp: 72° C.
γ₁: 79 mPa.s.

Example 14

| Category | Liquid crystal monomer codes | Content (%) |
|---|---|---|
| II | 3CC2 | 5 |
| II | 3CCV | 45 |
| II | 3CBB2 | 5 |
| II | V2CBB(3F)3 | 5 |
| III | 5BBB(2F, 4F) | 8 |
| III | C(5)BB(3F, 5F)CF₂OB(3F, 4F, 5F) | 17 |
| III | 5BB(3F, 5F)BCF₂OB(3F, 4F, 5F) | 6 |
| III | H(5)BBB(3F)B(3F, 4F, 5F) | 1 |
| IV | 3CBB(2F, 3F)O2 | 3 |
| III | 3CBB(3F, 5F)BCF3 | 5 |
| I | | 0.05 |

-continued

| Category | Liquid crystal monomer codes | Content (%) |
|---|---|---|

Δε [1 KHz, 20° C.]: 6.5
Δn [589 nm, 20° C.]: 0.11
Cp: 72° C.
γ₁: 75 mPa.s.

Example 15

| Category | Liquid crystal monomer codes | Content (%) |
|---|---|---|
| II | 3CC2 | 10 |
| II | 3CCB(3F)O1 | 6 |
| II | 3CCBO1 | 6 |
| II | 1BB5 | 8 |
| II | 3CBO2 | 6 |
| II | 3CCB(3F)2 | 5 |
| II | 3CBB1 | 6 |
| IV | 3CBB(2F, 3F)O2 | 8 |
| IV | 2CBB(2F, 3F)O2 | 12 |
| IV | 3C1OB(2F, 3F)O2 | 10 |
| IV | C(5)BB(2F, 3F)O2 | 10 |
| III | 5BBB(2F, 4F) | 13 |
| I | | 0.1 |

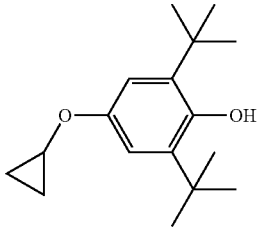

Δε [1 KHz, 20° C.]: −3.4
Δn [589 nm, 20° C.]: 0.12
Cp: 76° C.
γ₁: 95 mPa.s.

Example 16

| Category | Liquid crystal monomer codes | Content (%) |
|---|---|---|
| II | 3CC2 | 23 |
| II | 3CCV1 | 12 |
| III | 5BBB(2F, 4F) | 7 |
| III | 3BBB(2F, 4F) | 7 |
| II | 2CBB2 | 9 |
| II | 3CBB2 | 5 |
| IV | 3CB(2F, 3F)BO2 | 8 |
| IV | 2CBB(2F, 3F)O2 | 12 |
| IV | 3C1OB(2F, 3F)O2 | 10 |
| IV | C(5)1OSaO4 | 6 |
| I | | 0.02 |

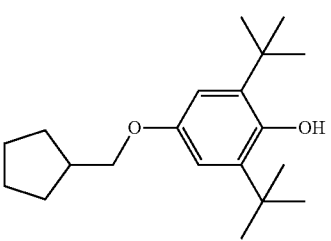

-continued

| Category | Liquid crystal monomer codes | Content (%) |
|---|---|---|

Δε [1 KHz, 20° C.]: −3.0
Δn [589 nm, 20° C.]: 0.115
Cp: 97° C.
γ₁: 110 mPa.s.

Example 17

| Category | Liquid crystal monomer codes | Content (%) |
|---|---|---|
| II | 3CC2 | 20 |
| II | 3CCV | 18 |
| II | 3CBO2 | 2 |
| II | VCCB1 | 10 |
| IV | 3CCB(2F, 3F)O2 | 8 |
| IV | 2CB(2F, 3F)B(3F)O2 | 12 |
| IV | 3C1OB(2F, 3F)O2 | 10 |
| IV | C(5)BB(2F, 3F)O2 | 10 |
| IV | 3CB(2F, 3F)O2 | 10 |
| I | | 0.005 |

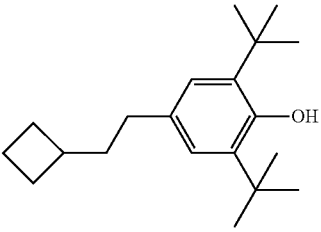 [SMILES: CC(C)(C)c1cc(CCC2CCC2)cc(C(C)(C)C)c1O]

Δε [1 KHz, 20° C.]: −3.5
Δn [589 nm, 20° C.]: 0.08
Cp: 60° C.
γ₁: 90 mPa.s.

Example 18

| Category | Liquid crystal monomer codes | Content (%) |
|---|---|---|
| II | 3CC2 | 30 |
| II | 3CCV | 20 |
| II | VCCBO2 | 2 |
| II | V2CCB(3F)3 | 3 |
| IV | VCCB(2F, 3F)O2 | 8 |
| IV | 2CBB(2F, 3F)O2 | 12 |
| IV | 3C1OB(2F, 3F)O2 | 10 |
| IV | C(5)CB(2F, 3F)O2 | 10 |
| IV | 3CB(2F, 3F)O2 | 5 |
| I | | 0.3 |

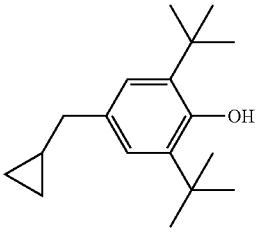 [SMILES: CC(C)(C)c1cc(CC2CC2)cc(C(C)(C)C)c1O]

Δε [1 KHz, 20° C.]: −3.0
Δn [589 nm, 20° C.]: 0.08/
Cp: 60° C.
γ₁: 82 mPa.s.

It can be seen from the above examples that the liquid crystal composition of the present invention has a lower rotary viscosity $\gamma_1$, is used for liquid crystal display, can achieve a quick response, and further has a moderate dielectric anisotropy $\Delta\varepsilon$, a moderate optical anisotropy $\Delta n$, and a high stability to heat. It is especially suitable for liquid crystal materials for TN, IPS, and VA modes.

The invention claimed is:

1. A liquid crystal composition comprising
a stabilizer represented by formula I, and,
one or more of compounds represented by formulas II-1 to II-14,

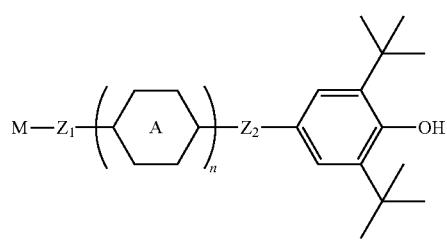

I wherein M represents cyclopentyl, cyclobutyl or cyclopropyl;
$Z_1$ and $Z_2$ each independently represent a single bond;

represents one or two of

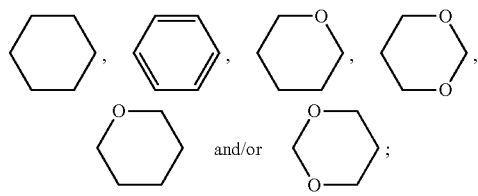

and
n represents 1 or 2;

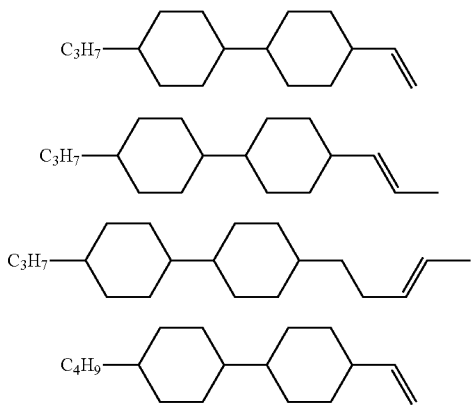

II-1

II-2

II-3

II-4

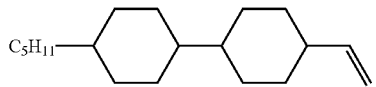

II-5

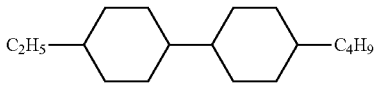

II-6

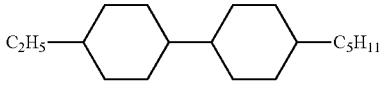

II-7

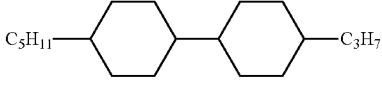

II-8

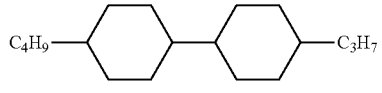

II-9

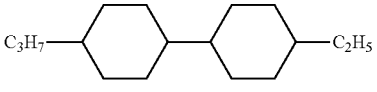

II-10

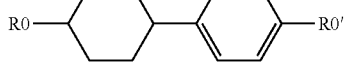

II-11

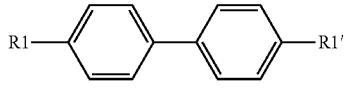

II-12

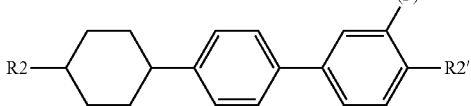

II-13

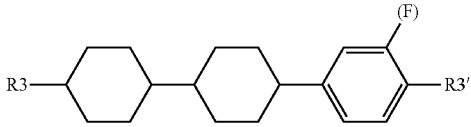

II-14 wherein R0, R0', R1, R1', R2, R2', R3, R3' each independently represent an alkyl group having a carbon atom number of 1-10, an alkenyl group having a carbon atom number of 2-10, or an alkoxy group having a carbon atom number of 1-10, wherein any —CH$_2$— can be substituted by —O—, and any hydrogen can be substituted by F; and
the (F)s each independently represent H or F.

2. The liquid crystal composition according to claim 1, characterized in that said stabilizer represented by formula I is selected from the following structures:

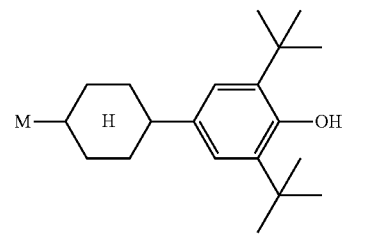
I-a
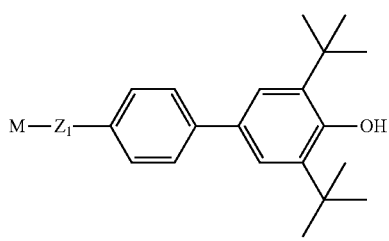
I-b
wherein M represents cyclopentyl, cyclobutyl or cyclopropyl;
represents
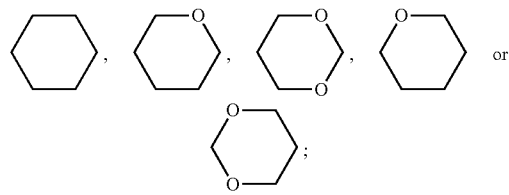
or
;
and
$Z_1$ represents a single bond.
3. The liquid crystal composition according to claim 2, characterized in that said stabilizer represented by formula I-a is selected from the following structures:
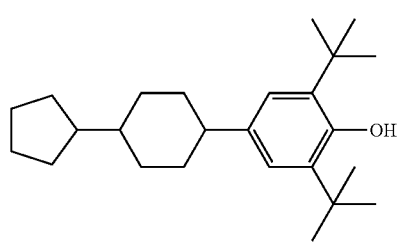
I-a-1
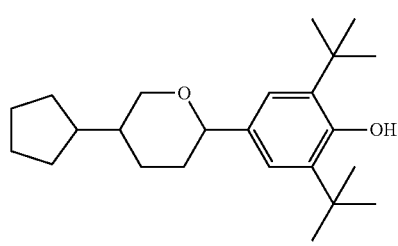
I-a-3
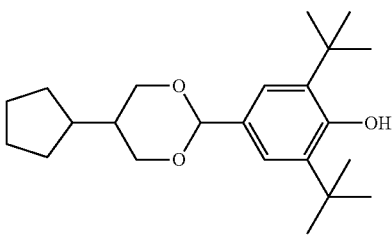
I-a-4
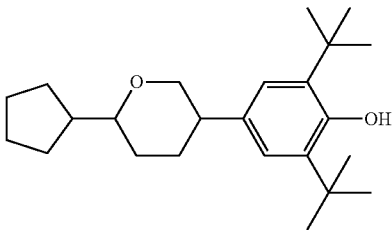
I-a-5
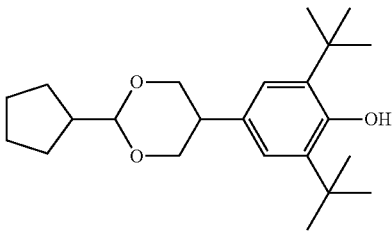
I-a-6
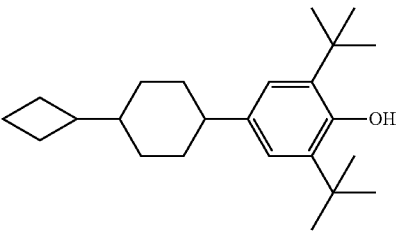
I-a-7
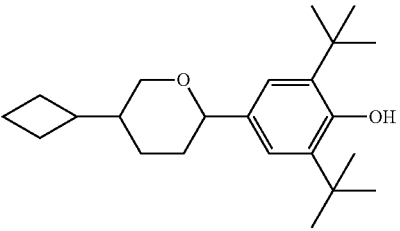
I-a-9
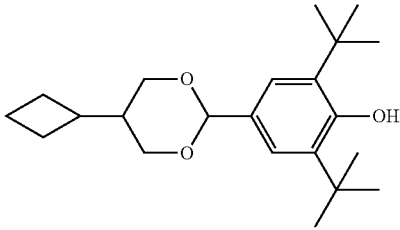
I-a-10

I-a-11 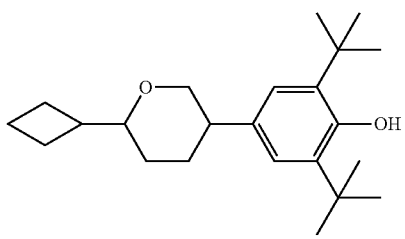

I-a-12 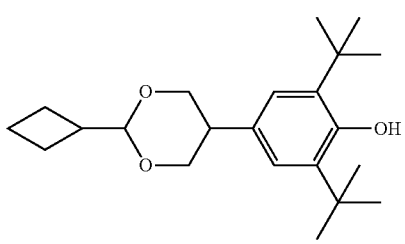

I-a-13 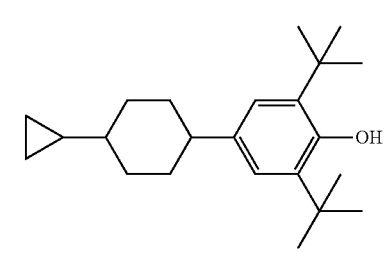

I-a-15 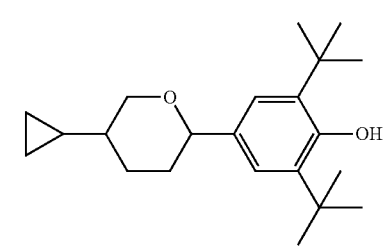

I-a-16 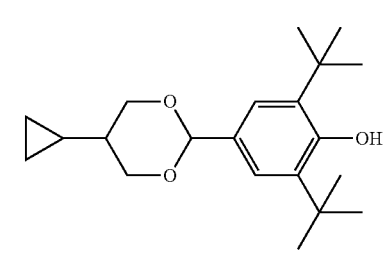

I-a-17 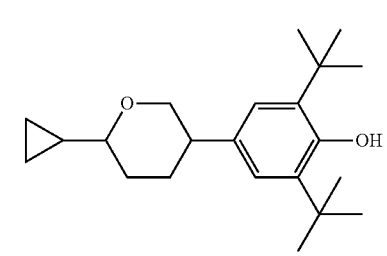

I-a-18 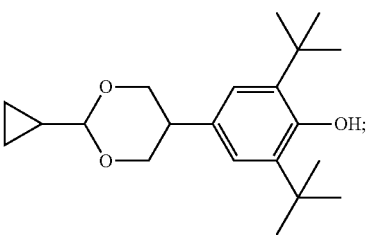

said stabilizer represented by formula I-b is selected from the following structures:

I-b-1 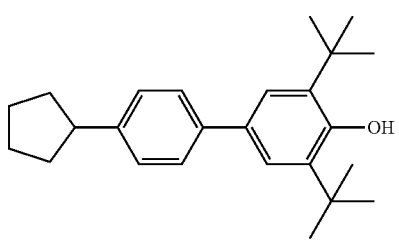

I-b-2 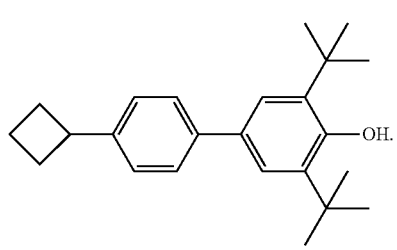

4. The liquid crystal composition according to claim 1, characterized in that in said liquid crystal composition, the total content in mass percentage of the compound represented by formula I is 0.001-5%; the total content in mass percentage of the compounds represented by formulas II-1 to II-10 is 1-60%; and the total content in mass percentage of the compounds represented by formulas II-11 to 11-14 is 0-30%;

wherein R0 and R2 each independently represent an alkyl group having a carbon atom number of 1-5 or an alkenyl group having a carbon atom number of 2-5, and R1 and R3 each independently represent an alkyl or alkoxy group having a carbon atom number of 1-5.

5. The liquid crystal composition according to claim 1, characterized in that said liquid crystal composition is a positive liquid crystal composition and further comprises one or more compounds represented by formula III:

III

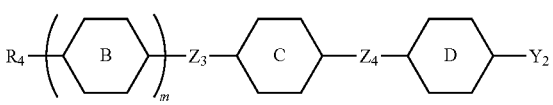

wherein $R_4$ represents an alkyl group having a carbon atom number of 1-10, a fluorinated alkyl group having a carbon atom number of 1-10, an alkoxy group having a carbon atom number of 1-10, a fluorinated alkoxy group having a carbon atom number of 1-10, an alkenyl group having a carbon atom number of 2-10, a fluorinated alkenyl group having a carbon atom number of 2-10, an alkenoxy group having a carbon atom number of 3-8 or a fluorinated alkenoxy group having a carbon atom number of 3-8, and any one or more $CH_2$ in $R_4$ may be substituted by cyclopentyl, cyclobutyl or cyclopropyl;

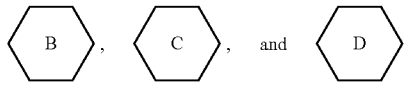

each independently represent
one or two of

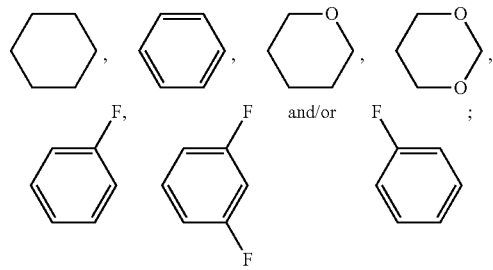

m represents 1 or 2;
$Z_3$ and $Z_4$ each independently represent a single bond, $-CF_2O-$, $-CH_2CH_2-$ or $-CH_2O-$; and
$Y_2$ represents F, a fluorinated alkyl group having a carbon atom number of 1-5, a fluorinated alkoxy group having a carbon atom number of 1-5, a fluorinated alkenyl group having a carbon atom number of 2-5, or a fluorinated alkenoxy group having a carbon atom number of 3-8.

6. The liquid crystal composition according to claim 5, characterized in that said one or more compounds represented by formula III are one or more of compounds represented by formulas III-1 to III-22:

III-1
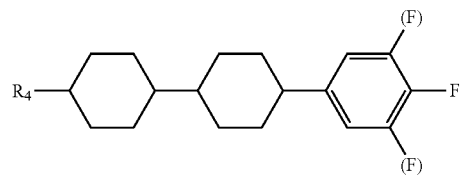

III-2
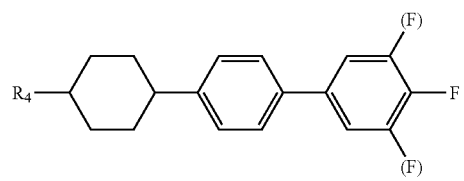

III-3
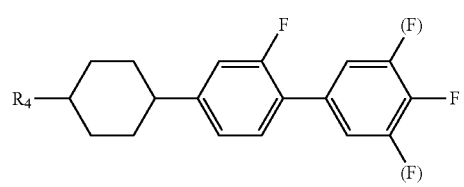

III-4
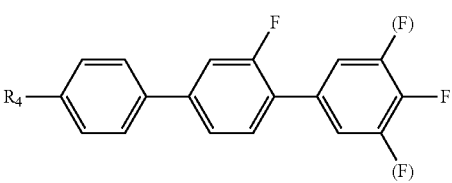

III-5
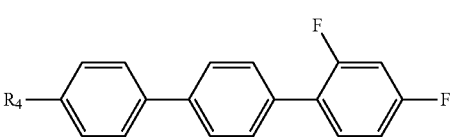

III-6
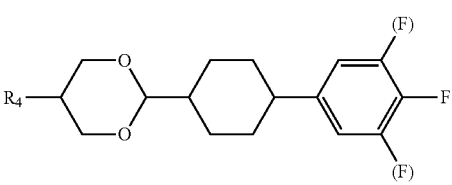

III-7
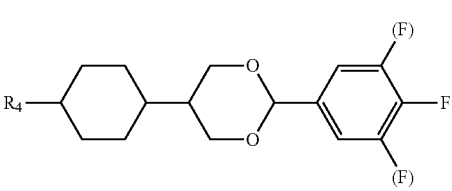

III-8
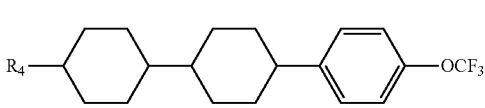

III-9
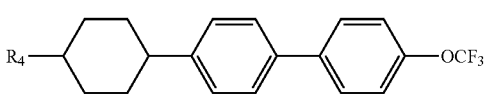

III-10
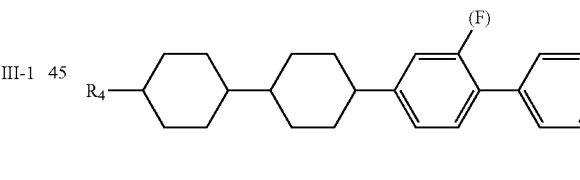

III-11
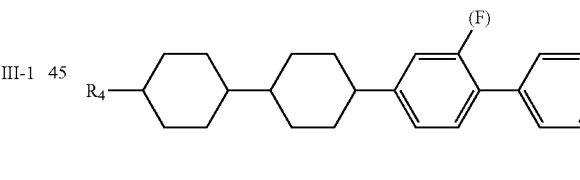

III-12
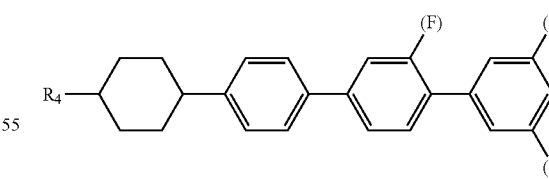

-continued

III-13

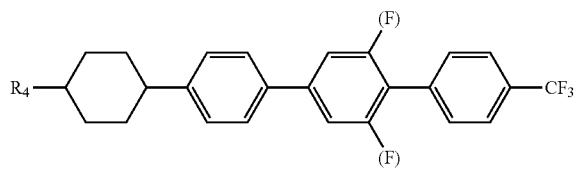

III-14

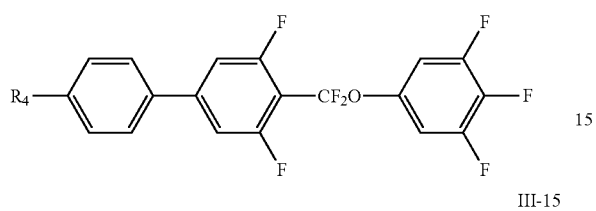

III-15

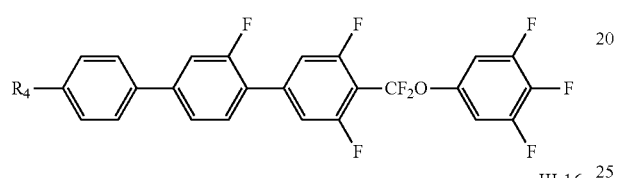

III-16

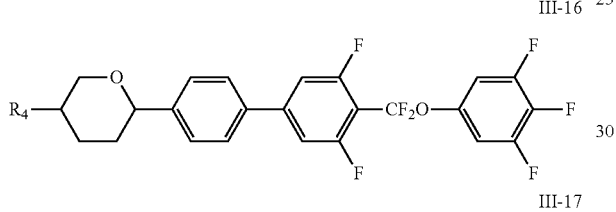

III-17

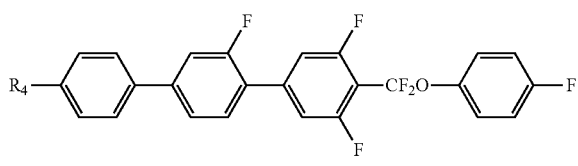

III-18

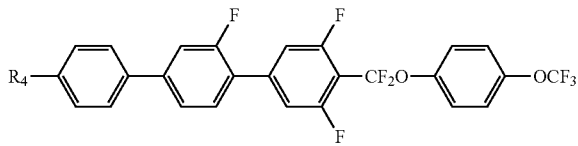

III-19

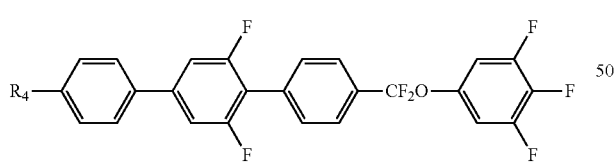

III-20

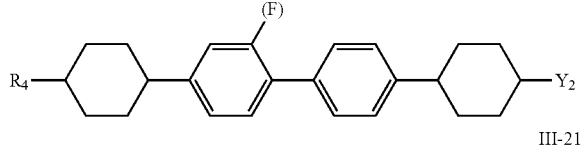

III-21

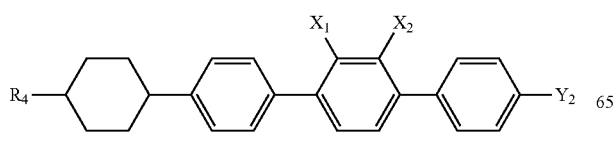

III-22

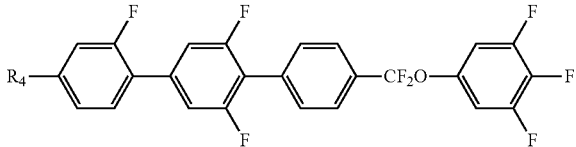

wherein $X_1$ and $X_2$ each independently represent H or F, and cannot both be F or H;

$R_4$ each independently represents an alkyl group having a carbon atom number of 1-10, a fluorinated alkyl group having a carbon atom number of 1-10, an alkoxy group having a carbon atom number of 1-10, a fluorinated alkoxy group having a carbon atom number of 1-10, an alkenyl group having a carbon atom number of 2-10, a fluorinated alkenyl group having a carbon atom number of 2-10, an alkenoxy group having a carbon atom number of 3-8 or a fluorinated alkenoxy group having a carbon atom number of 3-8, and any $CH_2$ in $R_4$ may be substituted by cyclopentyl, cyclobutyl or cyclopropyl;

the (F)s each independently represent H or F; and $Y_2$ each independently represents F, a fluorinated alkyl group having a carbon atom number of 1-5, a fluorinated alkoxy group having a carbon atom number of 1-5, a fluorinated alkenyl group having a carbon atom number of 2-5, or a fluorinated alkenoxy group having a carbon atom number of 3-8.

7. The liquid crystal composition according to claim 1, characterized in that said liquid crystal composition is a negative liquid crystal composition and further comprises one or more compounds represented by formula IV:

IV

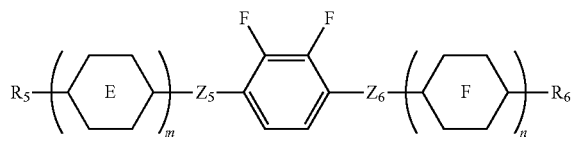

wherein $R_5$ and $R_6$ each independently represent an alkyl group having a carbon atom number of 1-10, a fluorinated alkyl group having a carbon atom number of 1-10, an alkoxy group having a carbon atom number of 1-10, a fluorinated alkoxy group having a carbon atom number of 1-10, an alkenyl group having a carbon atom number of 2-10, a fluorinated alkenyl group having a carbon atom number of 2-10, an alkenoxy group having a carbon atom number of 3-8 or a fluorinated alkenoxy group having a carbon atom number of 3-8, and any $CH_2$ in $R_5$ and $R_6$ may be substituted by cyclopentyl, cyclobutyl or cyclopropyl;

$Z_5$ and $Z_6$ each independently represent a single bond, —$CH_2CH_2$—, —$CH_2O$—;

 and 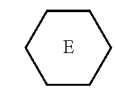

each independently represent one of

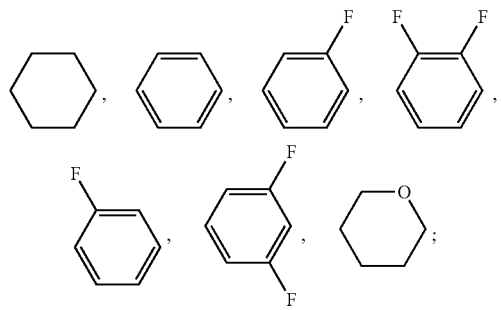

m represents 1 or 2; and n represents 0, 1 or 2.

8. The liquid crystal composition according to claim 7, characterized in that said one or more compounds represented by formula IV are one or more of compounds represented by formulas IV-1 to IV-11:

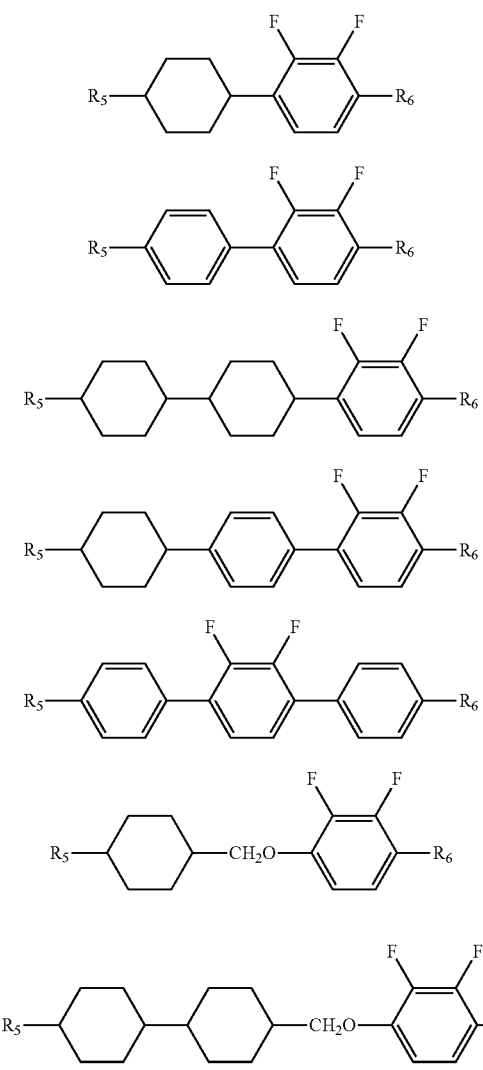

wherein $R_5$ and $R_6$ each independently represent an alkyl group having a carbon atom number of 1-10, a fluorinated alkyl group having a carbon atom number of 1-10, an alkoxy group having a carbon atom number of 1-10, a fluorinated alkoxy group having a carbon atom number of 1-10, an alkenyl group having a carbon atom number of 2-10, a fluorinated alkenyl group having a carbon atom number of 2-10, an alkenoxy group having a carbon atom number of 3-8 or a fluorinated alkenoxy group having a carbon atom number of 3-8, and any $CH_2$ in $R_5$ and $R_6$ may be substituted by cyclopentyl, cyclobutyl or cyclopropyl.

9. The liquid crystal composition according to claim 1, characterized in that said liquid crystal composition is a negative liquid crystal composition and further comprises one or more compounds represented by formula V:

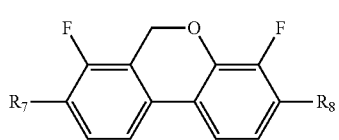

wherein $R_7$ and $R_8$ each independently represent an alkyl group having a carbon atom number of 1-10, a fluorinated alkyl group having a carbon atom number of 1-10, an alkoxy group having a carbon atom number of 1-10, a fluorinated alkoxy group having a carbon atom number of 1-10, an alkenyl group having a carbon atom number of 2-10, a fluorinated alkenyl group having a carbon atom number of 2-10, an alkenoxy group having a carbon atom number of 3-8 or a fluorinated alkenoxy group having a carbon atom number of 3-8, and any $CH_2$ in $R_7$ and $R_8$ may be substituted by cyclopentyl, cyclobutyl or cyclopropyl.

10. The liquid crystal composition according to claim 4, characterized in that said liquid crystal composition is a negative liquid crystal composition and further comprises one or more compounds represented by formula V:

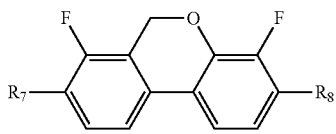

wherein $R_7$ and $R_8$ each independently represent an alkyl group having a carbon atom number of 1-10, a fluorinated alkyl group having a carbon atom number of 1-10, an alkoxy group having a carbon atom number of 1-10, a fluorinated alkoxy group having a carbon atom number of 1-10, an alkenyl group having a carbon atom number of 2-10, a fluorinated alkenyl group having a carbon atom number of 2-10, an alkenoxy group having a carbon atom number of 3-8 or a fluorinated alkenoxy group having a carbon atom number of 3-8, and any $CH_2$ in $R_7$ and $R_8$ may be substituted by cyclopentyl, cyclobutyl or cyclopropyl.

11. The liquid crystal composition according to claim 7, characterized in that said liquid crystal composition is a negative liquid crystal composition and further comprises one or more compounds represented by formula V:

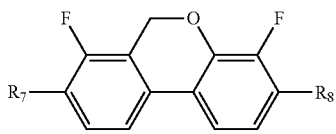

wherein $R_7$ and $R_8$ each independently represent an alkyl group having a carbon atom number of 1-10, a fluorinated alkyl group having a carbon atom number of 1-10, an alkoxy group having a carbon atom number of 1-10, a fluorinated alkoxy group having a carbon atom number of 1-10, an alkenyl group having a carbon atom number of 2-10, a fluorinated alkenyl group having a carbon atom number of 2-10, an alkenoxy group having a carbon atom number of 3-8 or a fluorinated alkenoxy group having a carbon atom number of 3-8, and any $CH_2$ in $R_7$ and $R_8$ may be substituted by cyclopentyl, cyclobutyl or cyclopropyl.

12. The liquid crystal composition according to claim 8, characterized in that said liquid crystal composition is a negative liquid crystal composition and further comprises one or more compounds represented by formula V:

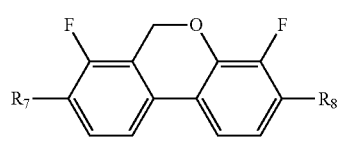

wherein $R_7$ and $R_8$ each independently represent an alkyl group having a carbon atom number of 1-10, a fluorinated alkyl group having a carbon atom number of 1-10, an alkoxy group having a carbon atom number of 1-10, a fluorinated alkoxy group having a carbon atom number of 1-10, an alkenyl group having a carbon atom number of 2-10, a fluorinated alkenyl group having a carbon atom number of 2-10, an alkenoxy group having a carbon atom number of 3-8 or a fluorinated alkenoxy group having a carbon atom number of 3-8, and any $CH_2$ in $R_7$ and $R_8$ may be substituted by cyclopentyl, cyclobutyl or cyclopropyl.

13. A liquid crystal display element or liquid crystal display comprising the liquid crystal composition of claim 1, characterized in that said liquid crystal display element or liquid crystal display is an active matrix display element or display or a passive matrix display element or display.

* * * * *